US012616389B2

(12) United States Patent
Ogawa et al.

(10) Patent No.: US 12,616,389 B2
(45) Date of Patent: May 5, 2026

(54) ESTIMATION SYSTEM, ESTIMATION METHOD, PROGRAM, ESTIMATION MODEL, BRAIN ACTIVITY TRAINING APPARATUS, BRAIN ACTIVITY TRAINING METHOD, AND BRAIN ACTIVITY TRAINING PROGRAM

(71) Applicants: ADVANCED TELECOMMUNICATIONS RESEARCH INSTITUTE INTERNATIONAL, Kyoto (JP); SHIONOGI & CO., LTD., Osaka (JP)

(72) Inventors: Takeshi Ogawa, Kyoto (JP); Ryuta Tamano, Kyoto (JP); Motoaki Kawanabe, Kyoto (JP); Mitsuo Kawato, Kyoto (JP)

(73) Assignees: ADVANCED TELECOMMUNICATIONS RESEARCH INSTITUTE INTERNATIONAL, Soraku-gun (JP); SHIONOGI & CO., LTD., Osaka (JP)

( * ) Notice: Subject to any disclaimer, the term of this patent is extended or adjusted under 35 U.S.C. 154(b) by 627 days.

(21) Appl. No.: 18/014,033

(22) PCT Filed: Jul. 1, 2021

(86) PCT No.: PCT/JP2021/024927
§ 371 (c)(1),
(2) Date: Dec. 30, 2022

(87) PCT Pub. No.: WO2022/004841
PCT Pub. Date: Jan. 6, 2022

(65) Prior Publication Data
US 2023/0293036 A1     Sep. 21, 2023

(30) Foreign Application Priority Data
Jul. 2, 2020     (JP) ................................. 2020-115053

(51) Int. Cl.
*A61B 5/055* (2006.01)
*A61B 5/369* (2021.01)

(52) U.S. Cl.
CPC .............. *A61B 5/055* (2013.01); *A61B 5/369* (2021.01); *A61B 2562/02* (2013.01)

(58) Field of Classification Search
CPC ......... A61B 5/055; A61B 5/369; A61B 5/372; A61B 5/375; A61B 2562/02
See application file for complete search history.

(56) References Cited

U.S. PATENT DOCUMENTS

2007/0252595 A1     11/2007 Volegov et al.
2014/0148657 A1     5/2014 Hendler et al.
(Continued)

FOREIGN PATENT DOCUMENTS

CN     105163659 A     12/2015
CN     105188528 A     12/2015
(Continued)

OTHER PUBLICATIONS

Gemein et al., "Machine-learning-based diagnostics of EEG pathology", May 26, 2020, NeuroImage, vol. 220, pp. 1-16 (Year: 2020).*
(Continued)

*Primary Examiner* — Joseph M Dietrich
(74) *Attorney, Agent, or Firm* — Birch, Stewart, Kolasch & Birch, LLP

(57) ABSTRACT

An estimation system obtains brain wave measurement data and functional magnetic resonance imaging measurement data simultaneously measured from a subject, calculates first functional connectivity for each channel combination based on correlation between channels included in the brain wave measurement data, calculates second functional connectivity for each brain network based on correlation between regions of interest included in the functional magnetic resonance
(Continued)

imaging measurement data, calculates a disorder-likelihood label by calculating a score representing disorder-likelihood to be estimated with the use of a plurality of second functional connectivities, and determines an estimation model for estimating disorder-likelihood based on prescribed first functional connectivity by machine learning using the first functional connectivity for each channel combination and the disorder-likelihood label.

18 Claims, 27 Drawing Sheets

(56)                References Cited

U.S. PATENT DOCUMENTS

| | | |
|---|---|---|
| 2015/0272461 A1 | 10/2015 | Morimoto et al. |
| 2015/0294074 A1 | 10/2015 | Kawato et al. |
| 2021/0035665 A1 | 2/2021 | Hirayama et al. |
| 2021/0401289 A1 | 12/2021 | Yamashita et al. |

FOREIGN PATENT DOCUMENTS

| | | |
|---|---|---|
| CN | 109820507 A | 5/2019 |
| CN | 110598793 A | 12/2019 |
| CN | 111132600 A | 5/2020 |
| JP | 6203324 B1 | 9/2017 |
| JP | 2017-192425 A | 10/2017 |
| JP | 2019-63377 A | 4/2019 |
| JP | 2019-93008 A | 6/2019 |
| JP | 2020-62369 A | 4/2020 |
| WO | WO 2018/162307 A1 | 9/2018 |

OTHER PUBLICATIONS

Chang et al., "EEG correlates of time-varying BOLD functional connectivity," Elsevier, NeuroImage, vol. 72, XP028995617, Jan. 31, 2013, pp. 227-236.

Extended European Search Report for European Application No. 21831592.7, dated Jun. 3, 2024.

Hosseini et al., "Deep Learning with Edge Computing for Localization of Epileptogenicity using Multmodal rs-fMRI and EEG Big Data," 2017 IEEE International Conference on Autonomic Computing (ICAC), IEEE, XP033139554, Jul. 17, 2017, pp. 83-92.

Bartók et al., "Cognitive functions in prepsychotic patients", Progress in Neuro-Psychopharmacology & Biological Psychiatry, vol. 29, 2005, pp. 621-625.

Drysdale et al., "Resting-state connectivity biomarkers define neurophysiological subtypes of depression", Nature Medicine, vol. 23, No. 1, 2017, pp. 28-38.

Hirayama et al. "SPLICE: Fully Tractable Hierarchical Extension of ICA with Pooling", Proceedings of Machine Learning Research, vol. 70, 2017, 10 pages.

Ichikawa et al., "Primary functional brain connections associated with melancholic major depressive disorder and modulation by antidepressants", Scientific Reports, vol. 10, No. 3542, 2020, 12 pages.

Murta et al., "Electrophysiological Correlates of the BOLD Signal for EEG-Informed fMRI", Human Brain Mapping, vol. 36, 2015, pp. 391-414.

Yamada et al., "Resting-State Functional Connectivity-Based Biomarkers and Functional MRI-Based Neurofeedback for Psychiatric Disorders: A Challenge for Developing Theranostic Biomarkers", International Journal of Neuropsychopharmacology, vol. 20, No. 10, 2017, pp. 769-781.

Yoshihara et al., "Overlapping but asymmetrical relationships between schizophrenia and autism revealed by brain connectivity", bioRxiv, <URL:https://doi.org/10.1101/403212>, 2018, pp. 1-34.

Chinese Office Action and Search Report for Chinese Application No. 202180046953.X, dated Jul. 1, 2025, with English translation of the Office Action.

Zhu, "Recognition of EEG and Functional Magnetic Resonance Signals Based on Deep Learning," Chinese Excellent Master Thesis Full Text Database Medical and Health Technology, Issue 1, Jan. 15, 2020, 73 pages total, with English abstract.

* cited by examiner

FIG.1

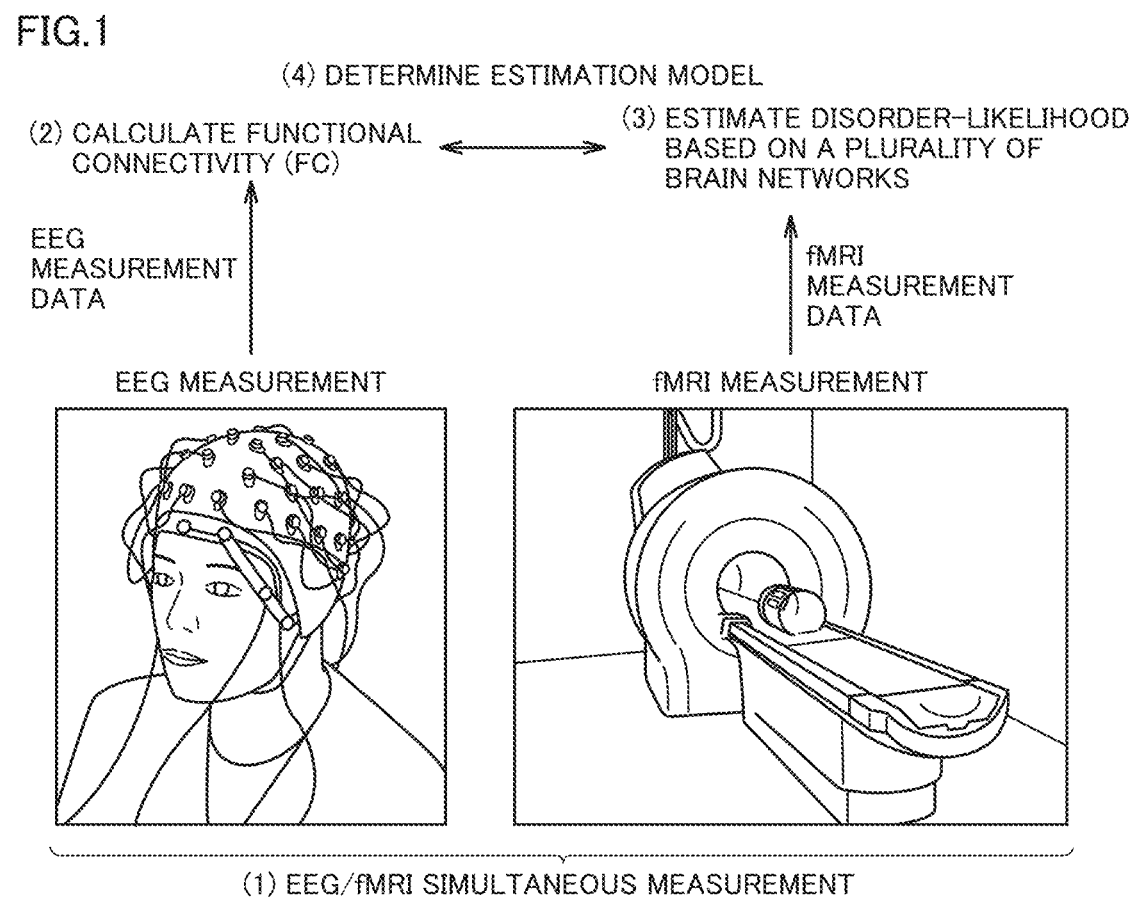

(4) DETERMINE ESTIMATION MODEL (2) CALCULATE FUNCTIONAL
CONNECTIVITY (FC)

(3) ESTIMATE DISORDER-LIKELIHOOD
BASED ON A PLURALITY OF
BRAIN NETWORKS

EEG
MEASUREMENT
DATA fMRI
MEASUREMENT
DATA

EEG MEASUREMENT fMRI MEASUREMENT (1) EEG/fMRI SIMULTANEOUS MEASUREMENT

FIG.4

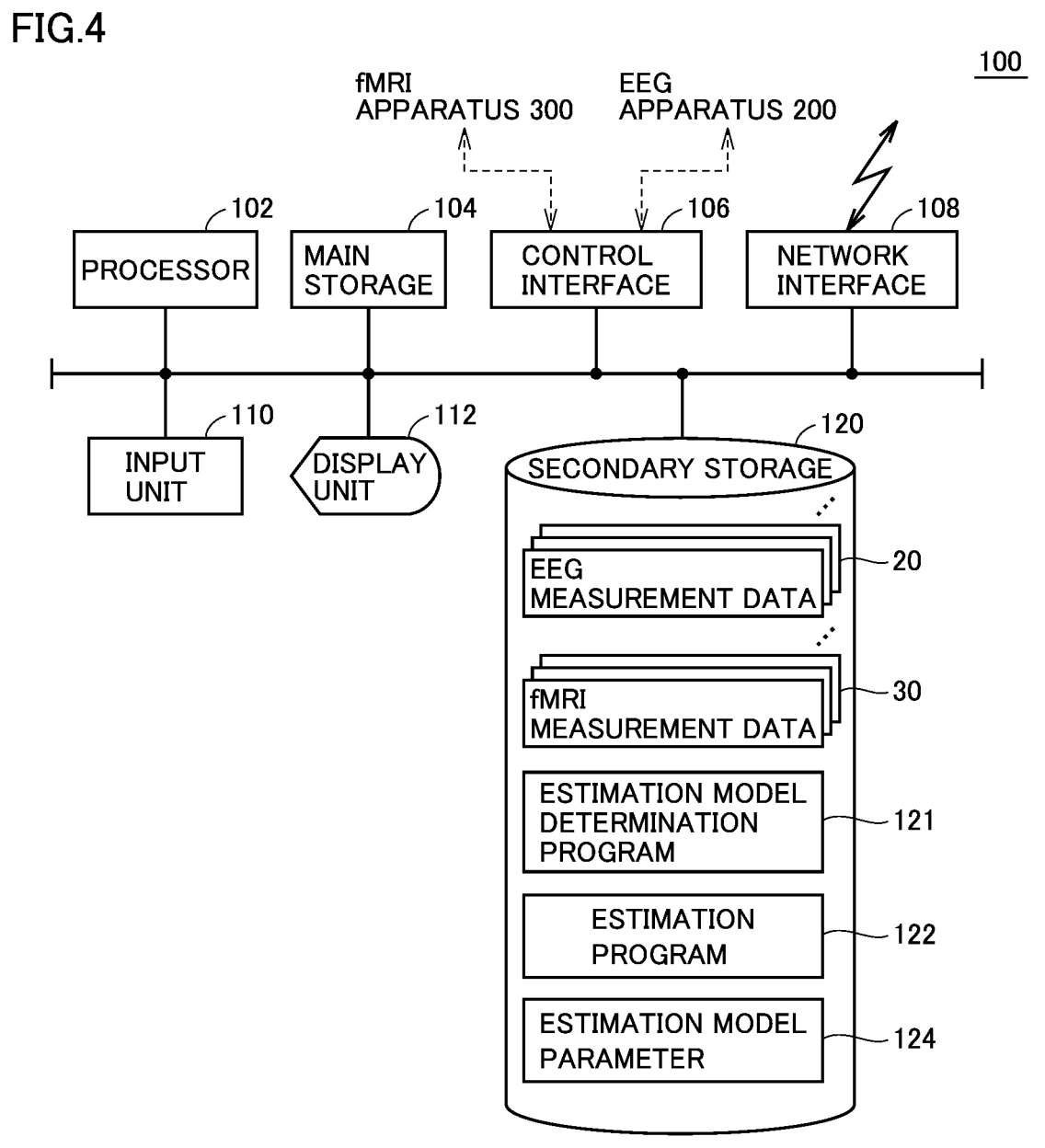

100 fMRI
APPARATUS 300

EEG
APPARATUS 200

| 102 | 104 | 106 | 108 |
|---|---|---|---|
| PROCESSOR | MAIN STORAGE | CONTROL INTERFACE | NETWORK INTERFACE |

110
INPUT UNIT

112
DISPLAY UNIT

120
SECONDARY STORAGE

EEG MEASUREMENT DATA — 20 fMRI MEASUREMENT DATA — 30

ESTIMATION MODEL DETERMINATION PROGRAM — 121

ESTIMATION PROGRAM — 122

ESTIMATION MODEL PARAMETER — 124

FIG.8

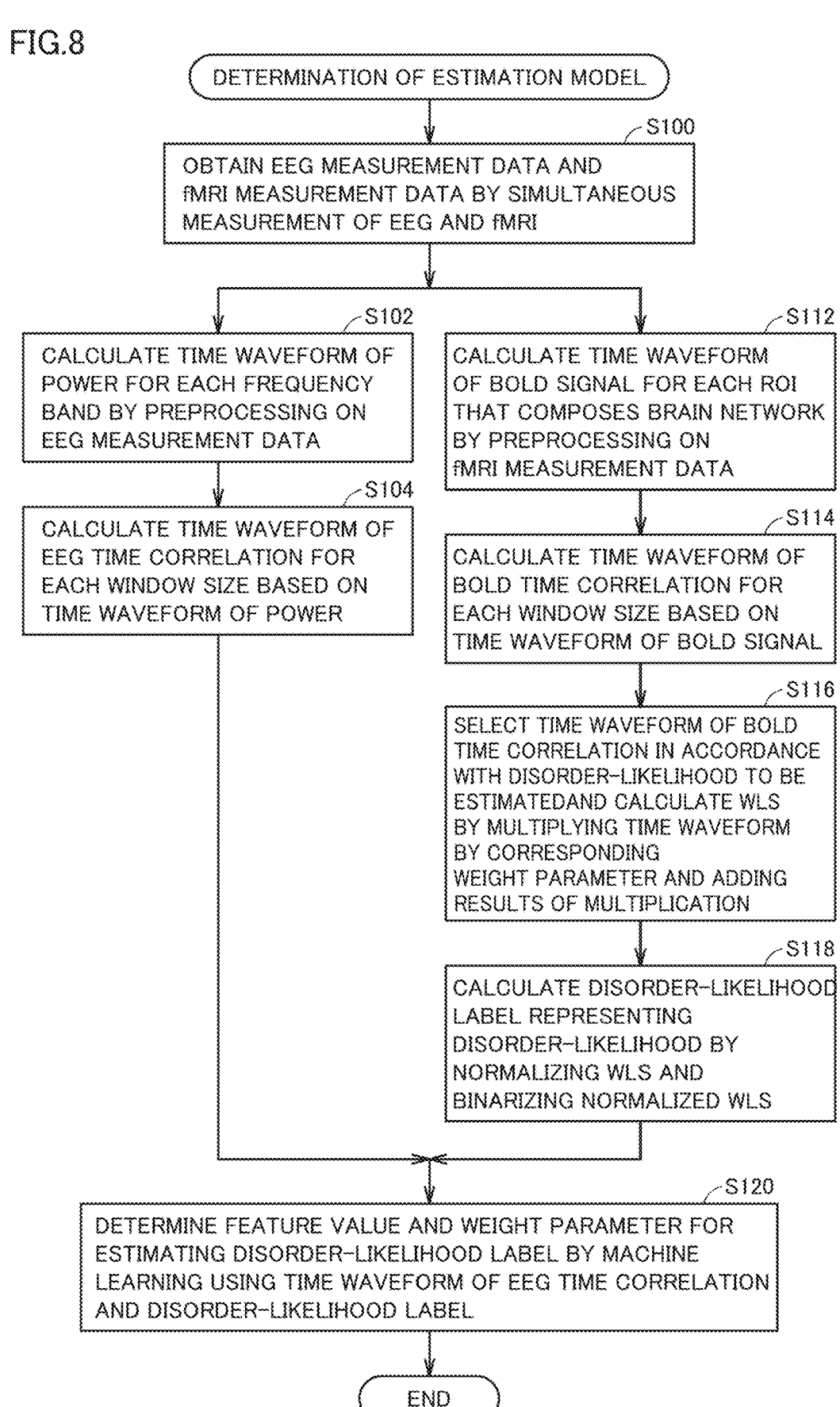

DETERMINATION OF ESTIMATION MODEL

S100
OBTAIN EEG MEASUREMENT DATA AND fMRI MEASUREMENT DATA BY SIMULTANEOUS MEASUREMENT OF EEG AND fMRI

S102
CALCULATE TIME WAVEFORM OF POWER FOR EACH FREQUENCY BAND BY PREPROCESSING ON EEG MEASUREMENT DATA

S104
CALCULATE TIME WAVEFORM OF EEG TIME CORRELATION FOR EACH WINDOW SIZE BASED ON TIME WAVEFORM OF POWER

S112
CALCULATE TIME WAVEFORM OF BOLD SIGNAL FOR EACH ROI THAT COMPOSES BRAIN NETWORK BY PREPROCESSING ON fMRI MEASUREMENT DATA

S114
CALCULATE TIME WAVEFORM OF BOLD TIME CORRELATION FOR EACH WINDOW SIZE BASED ON TIME WAVEFORM OF BOLD SIGNAL

S116
SELECT TIME WAVEFORM OF BOLD TIME CORRELATION IN ACCORDANCE WITH DISORDER-LIKELIHOOD TO BE ESTIMATEDAND CALCULATE WLS BY MULTIPLYING TIME WAVEFORM BY CORRESPONDING WEIGHT PARAMETER AND ADDING RESULTS OF MULTIPLICATION

S118
CALCULATE DISORDER-LIKELIHOOD LABEL REPRESENTING DISORDER-LIKELIHOOD BY NORMALIZING WLS AND BINARIZING NORMALIZED WLS

S120
DETERMINE FEATURE VALUE AND WEIGHT PARAMETER FOR ESTIMATING DISORDER-LIKELIHOOD LABEL BY MACHINE LEARNING USING TIME WAVEFORM OF EEG TIME CORRELATION AND DISORDER-LIKELIHOOD LABEL

END

FIG.11

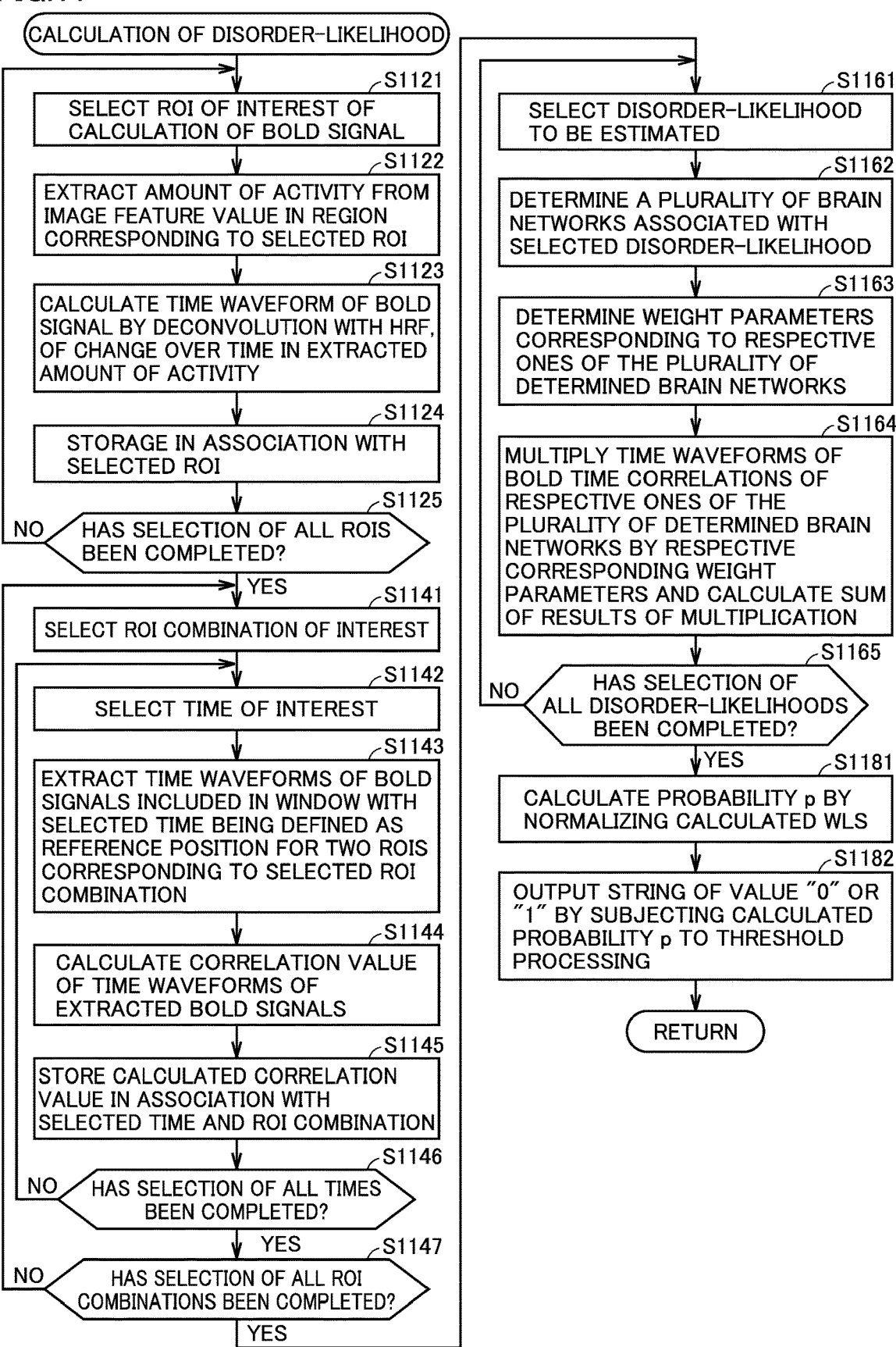

CALCULATION OF DISORDER-LIKELIHOOD

S1121
SELECT ROI OF INTEREST OF CALCULATION OF BOLD SIGNAL

S1122
EXTRACT AMOUNT OF ACTIVITY FROM IMAGE FEATURE VALUE IN REGION CORRESPONDING TO SELECTED ROI

S1123
CALCULATE TIME WAVEFORM OF BOLD SIGNAL BY DECONVOLUTION WITH HRF, OF CHANGE OVER TIME IN EXTRACTED AMOUNT OF ACTIVITY

S1124
STORAGE IN ASSOCIATION WITH SELECTED ROI

S1125
HAS SELECTION OF ALL ROIS BEEN COMPLETED?
NO
YES

S1141
SELECT ROI COMBINATION OF INTEREST

S1142
SELECT TIME OF INTEREST

S1143
EXTRACT TIME WAVEFORMS OF BOLD SIGNALS INCLUDED IN WINDOW WITH SELECTED TIME BEING DEFINED AS REFERENCE POSITION FOR TWO ROIS CORRESPONDING TO SELECTED ROI COMBINATION

S1144
CALCULATE CORRELATION VALUE OF TIME WAVEFORMS OF EXTRACTED BOLD SIGNALS

S1145
STORE CALCULATED CORRELATION VALUE IN ASSOCIATION WITH SELECTED TIME AND ROI COMBINATION

S1146
HAS SELECTION OF ALL TIMES BEEN COMPLETED?
NO
YES

S1147
HAS SELECTION OF ALL ROI COMBINATIONS BEEN COMPLETED?
NO
YES

S1161
SELECT DISORDER-LIKELIHOOD TO BE ESTIMATED

S1162
DETERMINE A PLURALITY OF BRAIN NETWORKS ASSOCIATED WITH SELECTED DISORDER-LIKELIHOOD

S1163
DETERMINE WEIGHT PARAMETERS CORRESPONDING TO RESPECTIVE ONES OF THE PLURALITY OF DETERMINED BRAIN NETWORKS

S1164
MULTIPLY TIME WAVEFORMS OF BOLD TIME CORRELATIONS OF RESPECTIVE ONES OF THE PLURALITY OF DETERMINED BRAIN NETWORKS BY RESPECTIVE CORRESPONDING WEIGHT PARAMETERS AND CALCULATE SUM OF RESULTS OF MULTIPLICATION

S1165
HAS SELECTION OF ALL DISORDER-LIKELIHOODS BEEN COMPLETED?
NO
YES

S1181
CALCULATE PROBABILITY p BY NORMALIZING CALCULATED WLS

S1182
OUTPUT STRING OF VALUE "0" OR "1" BY SUBJECTING CALCULATED PROBABILITY p TO THRESHOLD PROCESSING

RETURN

FIG.20
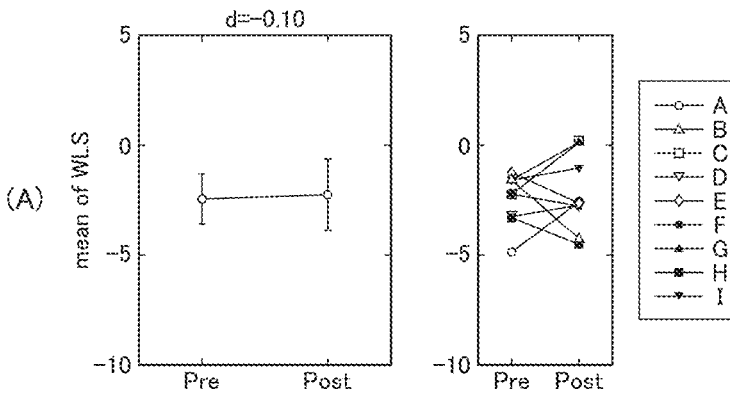
(A)
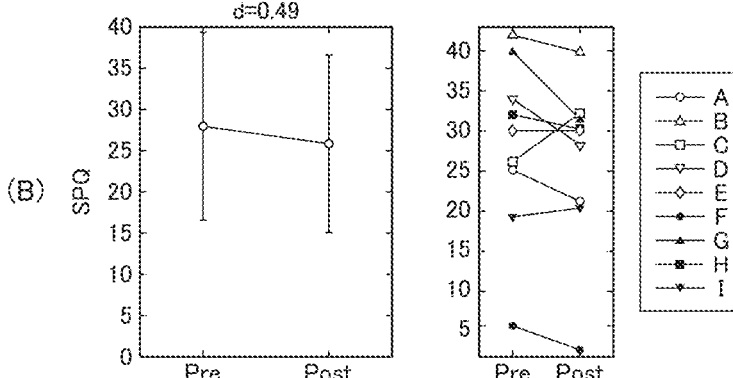
(B)
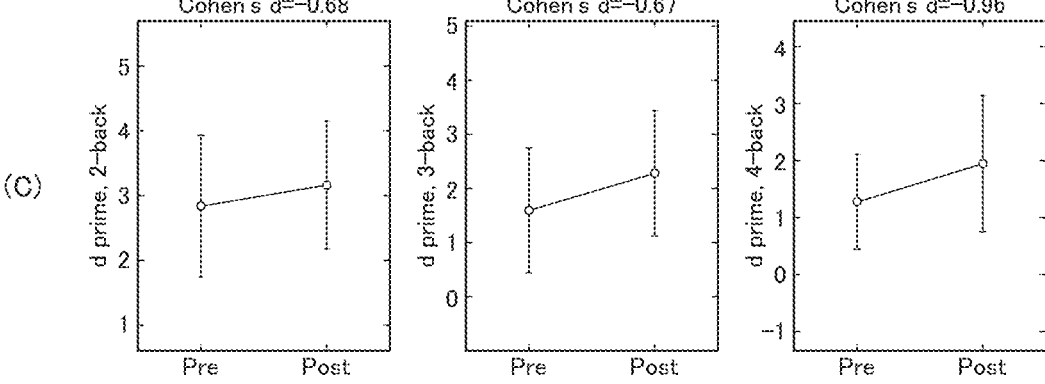
(C)

FIG.21
(A)
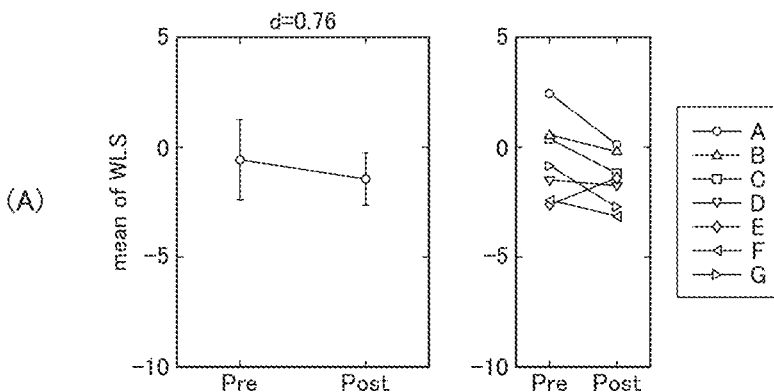
(B)
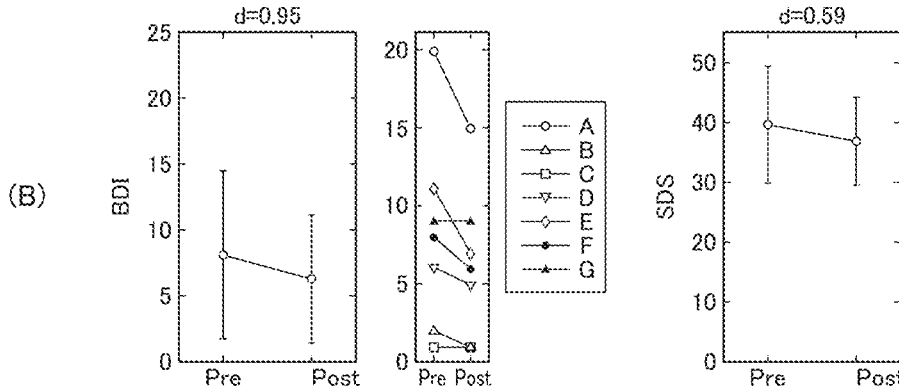
(C)
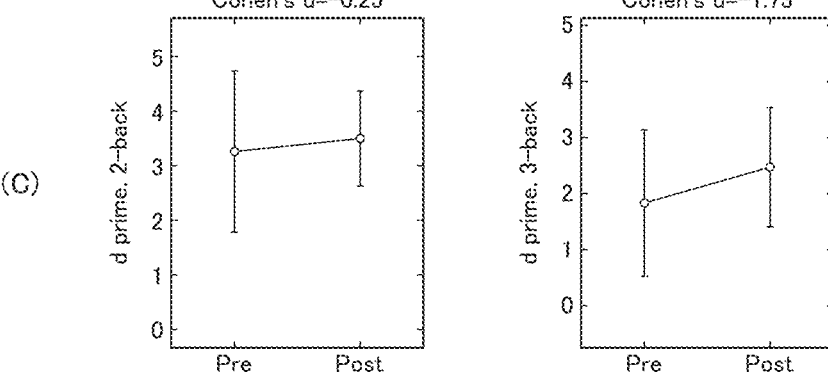

FIG.23
(A)
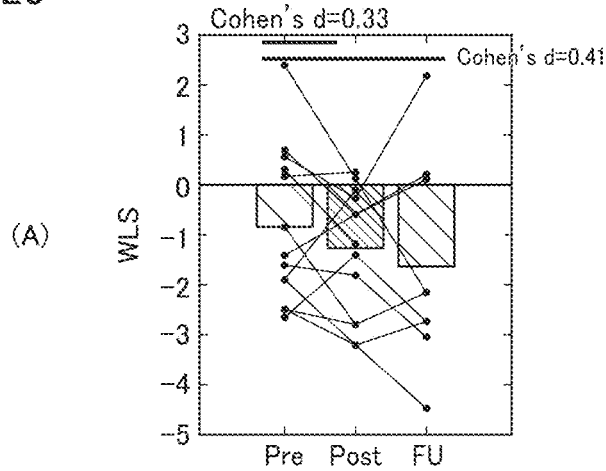
(B)
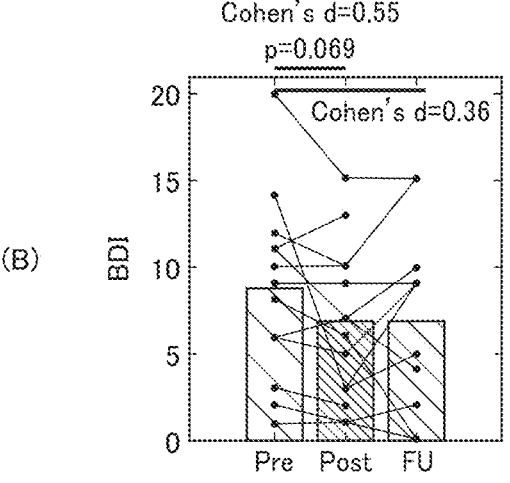
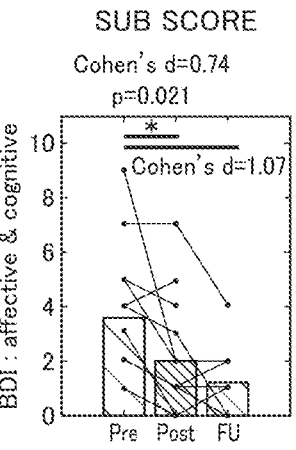
(C)
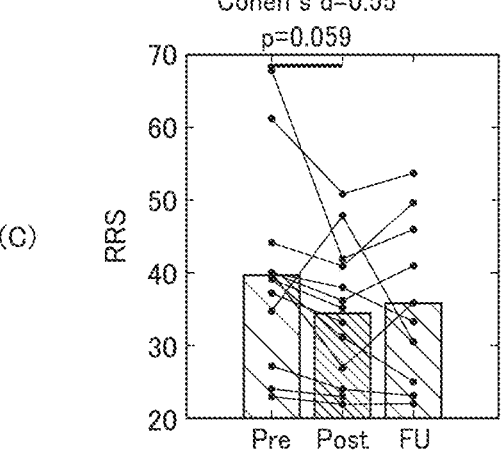
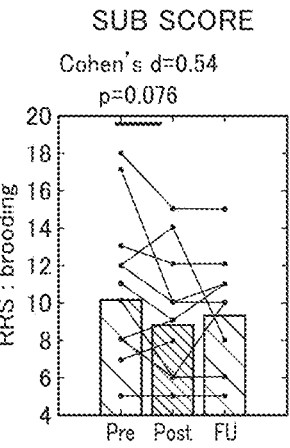

FIG.26
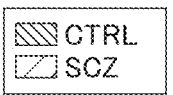
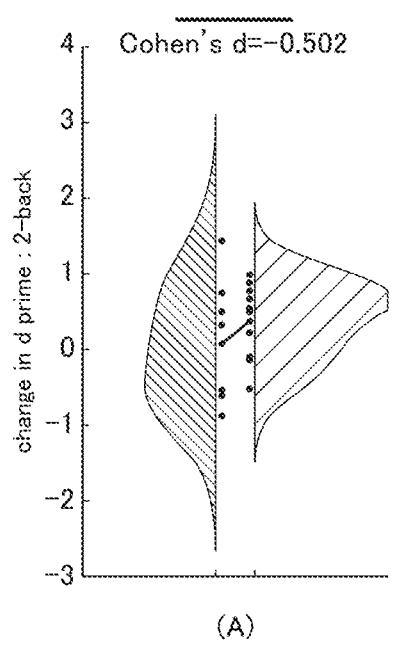
(A)
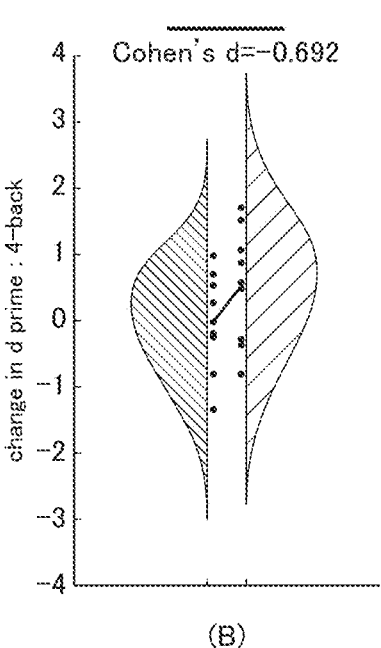
(B)
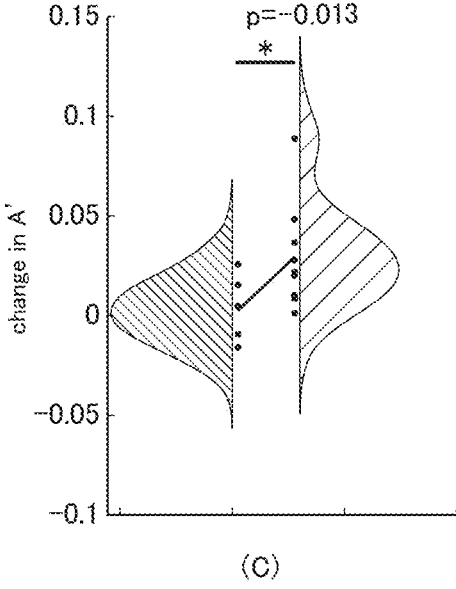
(C)
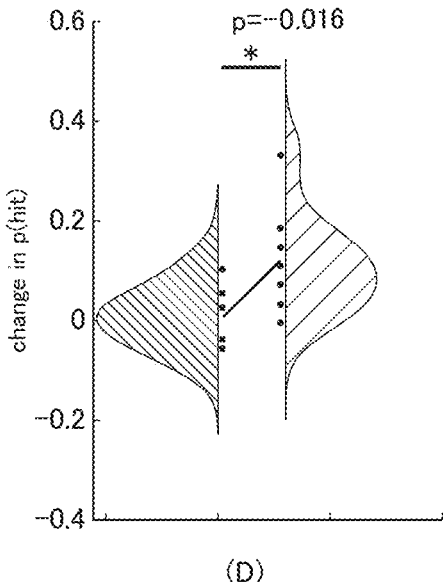
(D)

FIG.28
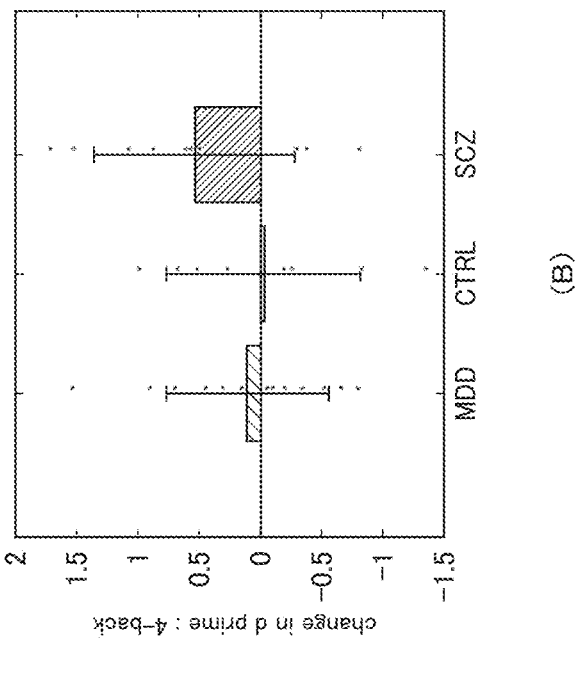
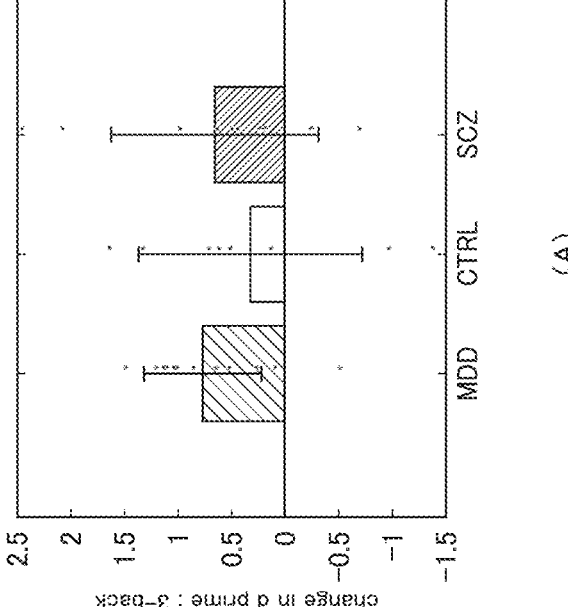

ESTIMATION SYSTEM, ESTIMATION METHOD, PROGRAM, ESTIMATION MODEL, BRAIN ACTIVITY TRAINING APPARATUS, BRAIN ACTIVITY TRAINING METHOD, AND BRAIN ACTIVITY TRAINING PROGRAM

TECHNICAL FIELD

The present invention relates to a technology for estimating disorder-likelihood based on measurement data on a brain activity.

BACKGROUND ART

Neurofeedback training or the like aiming at estimation of a brain function with the use of functional magnetic resonance imaging (which will also be abbreviated as "fMRI" below) representing one of techniques for non-invasive measurement of a brain activity and modulation of the brain function has been known. The neurofeedback training only with fMRI faces a challenge in viability such as cost.

Then, a method of combining an electromagnetic field measurement method such as electroencephalogram (which will also be abbreviated as "EEG" below) and fMRI has been proposed (see, for example, PTL 1 or the like). Variation in signal (a time waveform) measured in EEG is herein collectively referred to as "brain waves."

With the technique disclosed in PTL 1 or the like, an estimation model is created from measurement data obtained by simultaneous EEG and fMRI in a resting state (which will also be abbreviated as "EEG/fMRI simultaneous measurement data" below), and based on the created estimation model, neurofeedback is given using only EEG measurement data. EEG is more advantageous than other measurement techniques in terms of portability, mobility, a price, and possibility of prevalence. Therefore, by adopting the technique disclosed in PTL 1 or the like, cost can be reduced to thereby enhance viability of neurofeedback training.

It has been proposed to estimate an activity of each brain network based on fMRI measurement data in a resting state and to estimate "disorder-likelihood" based on a brain function expressed in a plurality of brain networks (see NPL 1 or the like). Estimation of "disorder-likelihood" is expected to be applied to diagnosis of psychiatric disorders, identification of a subtype of an identical disorder, and selection of a therapy.

CITATION LIST

Patent Literature

PTL 1: Japanese Patent Laying-Open No. 2019-093008

Non Patent Literature

NPL 1: Andrew T Drysdale et al., "Resting-state connectivity biomarkers define neurophysiological subtypes of depression," Nature Medicine, Volume 23, Number 1, pp. 28-38 (ISSN: 1546-170X), 2017. 1
NPL 2: Takashi Yamada et al., "Resting-State Functional Connectivity-Based Biomarkers and Functional MRI-Based Neurofeedback for Psychiatric Disorders: A Challenge for Developing Theranostic Biomarkers," International Journal of Neuropsychopharmacology (2017) 20 (10), pp. 769-781, 2017. 7. 17

NPL 3: Yujiro Yoshihara et al., "Overlapping but asymmetrical relationships between schizophrenia and autism revealed by brain connectivity," bioRxiv, <URL:https://doi.org/10.1101/403212>, 2018. 9. 7
NPL 4: Naho Ichikawa et al., "Primary functional brain connections associated with melancholic major depressive disorder and modulation by antidepressants," Scientific Reports (2020) 10:3542<URL:https://doi.org/10.1038/s41598-020-60527-z>, 2020
NPL 5: Enikö Bartók et al., "Cognitive functions in prepsychotic patients," Progress in Neuro-Psychopharmacology & Biological Psychiatry 29 (2005) 621-625

SUMMARY OF INVENTION

Technical Problem

Conventional neurofeedback training is directed to change in activity in a specific brain region or a specific brain network (change in time correlation of activities between a plurality of brain regions) (see, NPL 2).

A technique that allows easier estimation of any disorder associated with a plurality of brain networks has been demanded.

Solution to Problem

An estimation system according to one embodiment of the present invention includes obtaining means configured to obtain brain wave measurement data and functional magnetic resonance imaging measurement data simultaneously measured from a subject. The brain wave measurement data includes time waveforms for a plurality of channels corresponding to respective ones of a plurality of sensors arranged in a head of the subject. The estimation system includes first calculation means configured to calculate first functional connectivity for each channel combination based on correlation between channels included in the brain wave measurement data, second calculation means configured to calculate second functional connectivity for each brain network based on correlation between regions of interest included in the functional magnetic resonance imaging measurement data, third calculation means configured to calculate a disorder-likelihood label by calculating a score representing disorder-likelihood to be estimated based on a plurality of second functional connectivities, and machine learning means configured to determine an estimation model for estimating the disorder-likelihood based on prescribed first functional connectivity by machine learning using the first functional connectivity for each channel combination and the disorder-likelihood label.

The estimation system may further include estimation means configured to estimate disorder-likelihood of the subject by inputting the brain wave measurement data measured from the subject into the estimation model.

The estimation system may further include presentation means configured to calculate a second score in accordance with the estimated disorder-likelihood of the subject and present to the subject, information in accordance with the calculated second score.

The estimation model may be prepared for each disorder. At this time, an estimation model corresponding to a disorder that manifests in the subject may be applied to the subject.

Change in symptom of the subject may be assessed based on a second score in accordance with the estimated disorder-likelihood of the subject.

The third calculation means may calculate the score representing the disorder-likelihood based on a sum of results of multiplication of the plurality of second functional connectivities brought in correspondence with disorder-likelihood to be estimated by respective corresponding weight parameters.

The third calculation means may calculate the disorder-likelihood label by normalizing the score representing the disorder-likelihood and subject the normalized score to threshold processing.

The estimation model may include information for selecting first functional connectivity to be used for estimation among first functional connectivities for each channel combination and a weight parameter brought in correspondence with the selected first functional connectivity.

The first calculation means may calculate the first functional connectivity from a correlation value between time waveforms in a section included in a window set in common for time waveforms of brain waves in two channels of interest.

The first calculation means may calculate the first functional connectivity for each frequency band included in the brain wave measurement data and/or for each window size of a set window.

The estimation system may further include condition setting means configured to determine in advance in accordance with the subject, the frequency band included in the brain wave measurement data to be inputted to the estimation model and/or the window size.

The second calculation means may calculate the second functional connectivity from a correlation value between time waveforms in a section included in a window set in common for time waveforms indicating amounts of activities in two regions of interest.

An estimation method according to another embodiment of the present invention includes obtaining brain wave measurement data and functional magnetic resonance imaging measurement data simultaneously measured from a subject. The brain wave measurement data includes time waveforms for a plurality of channels corresponding to respective ones of a plurality of sensors arranged in a head of the subject. The estimation method includes calculating first functional connectivity for each channel combination based on correlation between channels included in the brain wave measurement data, calculating second functional connectivity for each brain network based on correlation between regions of interest included in the functional magnetic resonance imaging measurement data, calculating a disorder-likelihood label by calculating a score representing disorder-likelihood to be estimated based on a plurality of second functional connectivities, and determining an estimation model for estimating the disorder-likelihood based on prescribed first functional connectivity by machine learning using the first functional connectivity for each channel combination and the disorder-likelihood label.

A program according to yet another embodiment of the present invention causes a computer to perform obtaining brain wave measurement data and functional magnetic resonance imaging measurement data simultaneously measured from a subject. The brain wave measurement data includes time waveforms for a plurality of channels corresponding to respective ones of a plurality of sensors arranged in a head of the subject. The program causes the computer to perform calculating first functional connectivity for each channel combination based on correlation between channels included in the brain wave measurement data, calculating second functional connectivity for each brain network based on correlation between regions of interest included in the functional magnetic resonance imaging measurement data, calculating a disorder-likelihood label by calculating a score representing disorder-likelihood to be estimated based on a plurality of second functional connectivities, and determining an estimation model for estimating the disorder-likelihood based on prescribed first functional connectivity by machine learning using the first functional connectivity for each channel combination and the disorder-likelihood label.

According to yet another embodiment of the present invention, a trained estimation model for estimating disorder-likelihood of a subject based on brain wave measurement data measured from the subject is provided. Processing for constructing the estimation model includes obtaining brain wave measurement data and functional magnetic resonance imaging measurement data simultaneously measured from the subject. The brain wave measurement data includes time waveforms for a plurality of channels corresponding to respective ones of a plurality of sensors arranged in a head of the subject. Processing for constructing the estimation model includes calculating first functional connectivity for each channel combination based on correlation between channels included in the brain wave measurement data, calculating second functional connectivity for each brain network based on correlation between regions of interest included in the functional magnetic resonance imaging measurement data, calculating a disorder-likelihood label by calculating a score representing disorder-likelihood to be estimated based on a plurality of second functional connectivities, and determining the estimation model by machine learning using the first functional connectivity for each channel combination and the disorder-likelihood label.

According to yet another embodiment of the present invention, a brain activity training apparatus for conducting neurofeedback training is provided. The brain activity training apparatus includes a storage device where an estimation model for estimating disorder-likelihood of a subject generated before the neurofeedback training is conducted is stored and an electroencephalograph configured to measure brain wave measurement data of the subject in the neurofeedback training. The brain wave measurement data includes time waveforms for a plurality of channels corresponding to respective ones of a plurality of sensors arranged in a head of the subject. The brain activity training apparatus includes a presentation apparatus and a processing apparatus configured to calculate, in the neurofeedback training, disorder-likelihood of the subject with the estimation model based on measurement data from the electroencephalograph and outputs a signal for representation corresponding to the disorder-likelihood to the presentation apparatus.

The estimation model is generated by processing for obtaining brain wave measurement data and functional magnetic resonance imaging measurement data simultaneously measured from the subject, processing for calculating first functional connectivity for each channel combination based on correlation between channels included in the brain wave measurement data, processing for calculating second functional connectivity for each brain network based on correlation between regions of interest included in the functional magnetic resonance imaging measurement data, processing for calculating a disorder-likelihood label by calculating a score representing disorder-likelihood to be estimated based on a plurality of second functional connectivities, and processing for determining the estimation model by estimating the disorder-likelihood based on prescribed first functional connectivity by machine learning using the first functional connectivity for each channel combination and the disorder-likelihood label. The simultaneously measured brain wave measurement data includes a time waveform for each channel corresponding to each channel of the brain wave measurement data measured in the neurofeedback training.

According to yet another embodiment of the present invention, a brain activity training method for conducting neurofeedback training is provided. The brain activity training method includes obtaining an estimation model for estimating disorder-likelihood of a subject generated before the neurofeedback training is conducted and measuring brain wave measurement data of the subject in the neurofeedback training. The brain wave measurement data includes time waveforms for a plurality of channels corresponding to respective ones of a plurality of sensors arranged in a head of the subject. The brain activity training method includes calculating, in the neurofeedback training, disorder-likelihood of the subject with the estimation model based on the brain wave measurement data and outputting a signal for representation corresponding to the disorder-likelihood to a presentation apparatus. The obtaining an estimation model includes processing for obtaining brain wave measurement data and functional magnetic resonance imaging measurement data simultaneously measured from the subject, calculating first functional connectivity for each channel combination based on correlation between channels included in the brain wave measurement data, calculating second functional connectivity for each brain network based on correlation between regions of interest included in the functional magnetic resonance imaging measurement data, calculating a disorder-likelihood label by calculating a score representing disorder-likelihood to be estimated based on a plurality of second functional connectivities, and determining the estimation model by estimating the disorder-likelihood based on prescribed first functional connectivity by machine learning using the first functional connectivity for each channel combination and the disorder-likelihood label. The simultaneously measured brain wave measurement data includes a time waveform for each channel corresponding to each channel of the brain wave measurement data measured in the neurofeedback training.

According to yet another embodiment of the present invention, a brain activity training program for conducting neurofeedback training is provided. The brain activity training program causes a computer to perform storing an estimation model for estimating disorder-likelihood of a subject generated before the neurofeedback training is conducted and obtaining brain wave measurement data of the subject in the neurofeedback training. The brain wave measurement data includes time waveforms for a plurality of channels corresponding to respective ones of a plurality of sensors arranged in a head of the subject. The brain activity training program causes the computer to perform calculating, in the neurofeedback training, disorder-likelihood of the subject with the estimation model based on the brain wave measurement data and outputting a signal for representation corresponding to the disorder-likelihood to a presentation apparatus. The estimation model is generated by processing for obtaining brain wave measurement data and functional magnetic resonance imaging measurement data simultaneously measured from the subject, processing for calculating first functional connectivity for each channel combination based on correlation between channels included in the brain wave measurement data, processing for calculating second functional connectivity for each brain network based on correlation between regions of interest included in the functional magnetic resonance imaging measurement data, processing for calculating a disorder-likelihood label by calculating a score representing disorder-likelihood to be estimated based on a plurality of second functional connectivities, and processing for determining the estimation model by estimating the disorder-likelihood based on prescribed first functional connectivity by machine learning using the first functional connectivity for each channel combination and the disorder-likelihood label. The simultaneously measured brain wave measurement data includes a time waveform for each channel corresponding to each channel of the brain wave measurement data measured in the neurofeedback training.

Advantageous Effects of Invention

According to one embodiment of the present invention, any disorder associated with a plurality of brain networks can more easily be estimated.

BRIEF DESCRIPTION OF DRAWINGS

FIG. 1 is a schematic diagram showing overview of an estimation method according to the present embodiment.

FIG. 4 is a schematic diagram showing an exemplary hardware configuration of a processing apparatus included in the estimation system that performs the estimation method according to the present embodiment.

FIG. 8 is a flowchart showing a processing procedure in the estimation method according to the present embodiment.

FIG. 11 is a flowchart showing a more detailed processing procedure in steps S112 to S118 in FIG. 8.

FIG. 20 is a diagram showing an exemplary result of neurofeedback training in connection with schizophrenia (SCZ).

FIG. 21 is a diagram showing an exemplary result of neurofeedback training in connection with depression (MDD).

FIG. 23 is a diagram showing an exemplary long-term effect of neurofeedback training in connection with depression (MDD).

FIG. 26 is another diagram showing an effect of neurofeedback training in connection with schizophrenia (SCZ) as compared with the control group.

FIG. 28 is a diagram showing another experimental example for assessing specificity of the effect of neurofeedback training.

DESCRIPTION OF EMBODIMENTS

Figure 2:
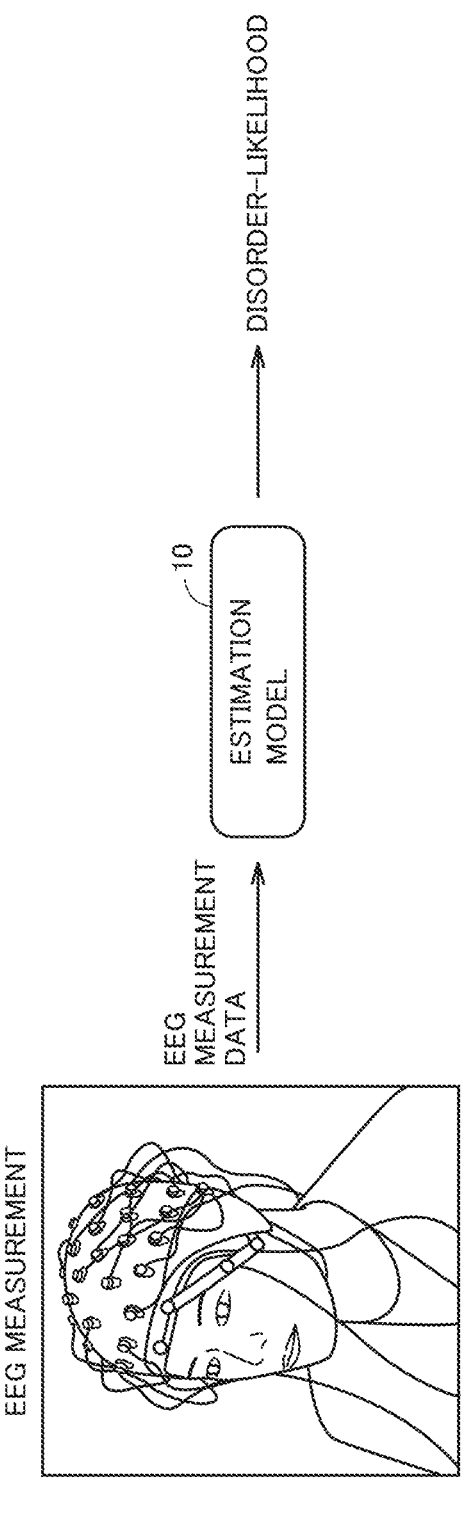
FIG. 2 is a schematic diagram showing overview of the estimation method according to the present embodiment.

An embodiment of the present invention will be described in detail with reference to the drawings. The same or corresponding elements in the drawings have the same reference characters allotted and description thereof will not be repeated.

A. Overview

Overview of an estimation method according to the present embodiment will initially be described. FIGS. 1 and 2 are schematic diagrams showing overview of the estimation method according to the present embodiment. FIG. 1 shows overview of processing (a learning phase) for determining an estimation model and FIG. 2 shows overview of processing (an estimation phase) for estimating disorder-likelihood with the determined estimation model.

The "disorder" herein is a term that encompasses not only sick symptoms of humans but also any mental or physical symptoms different from a condition that manifests in standard persons. A symptom that manifests in this case is also referred to as a "disorder-like symptom." "Disorder-likelihood" is a term that encompasses possibility (probability) that a subject of interest has a symptom corresponding to a "disorder" of interest and possibility (probability) that a symptom corresponding to a "disorder" of interest manifests in a subject of interest.

An "estimation model" herein is not limited to an estimation model to be used for estimation of such possibility, and it may also be used for estimation of possibility that a healthy person is in a state of a brain activity different by a prescribed extent or more from a standard "healthy brain activity state" (an extent of difference). In other words, the estimation model may also be used for estimation of a relative state of a brain activity.

"Functional connectivity" herein is a term that encompasses an indicator indicating a degree of functional connection between regions in the brain. The "functional connectivity" can be calculated with any method based on data measured with any measurement method. The method of calculating "functional connectivity" herein is not limited except for a case where specific measurement data and a specific calculation method are specified.

Referring to FIG. 1, in the estimation method in the present embodiment, initially, the same subject is simultaneously subjected to EEG and fMRI in a resting state to obtain EEG/fMRI simultaneous measurement data ((1) EEG/fMRI simultaneous measurement). At this time, data obtained by EEG (which will also be referred to as "EEG measurement data" below) and data obtained by fMRI (which will also be referred to as "fMRI measurement data" below) represent the same brain activities of the same subject. In other words, EEG/fMRI simultaneous measurement data includes brain wave measurement data (EEG measurement data) and measurement data of functional magnetic resonance imaging (fMRI measurement data) measured simultaneously from a subject.

Each sensor is typically composed of a pair of electrodes. Each sensor is also referred to as a channel and EEG measurement data corresponds to multiple-channel brain waves. In other words, EEG measurement data includes time waveforms for a plurality of channels corresponding to respective ones of a plurality of sensors arranged in a head of a subject. Functional connectivity in each frequency band is calculated from EEG measurement data ((2) calculate functional connectivity (FC)). The functional connectivity is also referred to as "FC" below.

In the estimation method according to the present embodiment, not only EEG representing a value of measurement of a voltage generated by electrical activities of a brain but also magnetoencephalography (MEG) representing a value of measurement of time-varying magnetic field generated by electrical activities of the brain can be used. For the sake of convenience of description, an example in which EEG measurement data is used will mainly be described in the description below.

fMRI measurement data is used for estimation of disorder-likelihood of a subject from a specific brain network. The brain network is also referred to as a resting state network (RSN), and it is a generic denotation of a characteristic brain activity pattern originating from a signal source belonging to a single brain region or coordination of signal sources belonging to a plurality of spatially distant brain regions. The brain network is defined mainly by fMRI in the resting state.

Specifically, seven types of (1) a control network (CON), (2) a dorsal attention network (DAN), (3) a default mode network (DMN), (4) a limbic system (LEVI), (5) a somatomotor network (SMN), (6) a ventral attention network (VAN), and (7) a visual network (VIS) have been known as the resting state networks.

The (1) control network (CON) may also be referred to as a frontal parietal network and the (6) ventral attention network (VAN) may also be referred to as a saliency network.

The resting state network described above may further be divided into some subnetworks. More specifically, the (1) control network (CON) is divided into three subnetworks, the (3) default mode network (DMN) is divided into four subnetworks, and each of other networks is divided into two subnetworks.

Disorder-likelihood of a subject is considered as being estimated based on one or more specific brain networks that have been known in advance for each disorder. Therefore, in the estimation method according to the present embodiment, disorder-likelihood of a subject is estimated based on one or more specific brain networks ((3) estimate disorder-likelihood based on a plurality of brain networks). In the description below, a result of threshold processing (by way of example, binarization processing) of disorder-likelihood is outputted. Therefore, a result of estimation is also referred to as a "disorder-likelihood label" (label). The disorder-likelihood label takes any of a plurality of values (labels).

Finally, an estimation model for estimating disorder-likelihood of a subject is determined by inputting EEG measurement data based on dynamic functional connectivity in each frequency band and disorder-likelihood of the subject ((4) determine estimation model). The estimation model corresponds to a kind of a trained model.

Referring to FIG. 2, EEG measurement data measured by EEG from a subject is inputted to a determined estimation model 10, so that a result of estimation of disorder-likelihood of the subject is outputted. With the result of estimation of disorder-likelihood of the subject, neurofeedback training (which will also simply be referred to as "training" below) or the like can be conducted. As will be described later, estimation model 10 includes also a function to select information suitable for estimation of disorder-likelihood from EEG measurement data measured by EEG from the subject.

Since a state of disorder-likelihood of the subject can successively be estimated with such estimation model 10, for example, neurofeedback can be realized with low cost. As will be described later, the estimation model has specificity depending on target thereof. Therefore, the estimation model is prepared for each disorder. Then, the estimation model corresponding to a disorder that manifests in a subject is applied.

B. Exemplary Hardware Configuration of Estimation System

An exemplary hardware configuration of an estimation system for realizing the estimation method according to the present embodiment will now be described.

Figure 3:
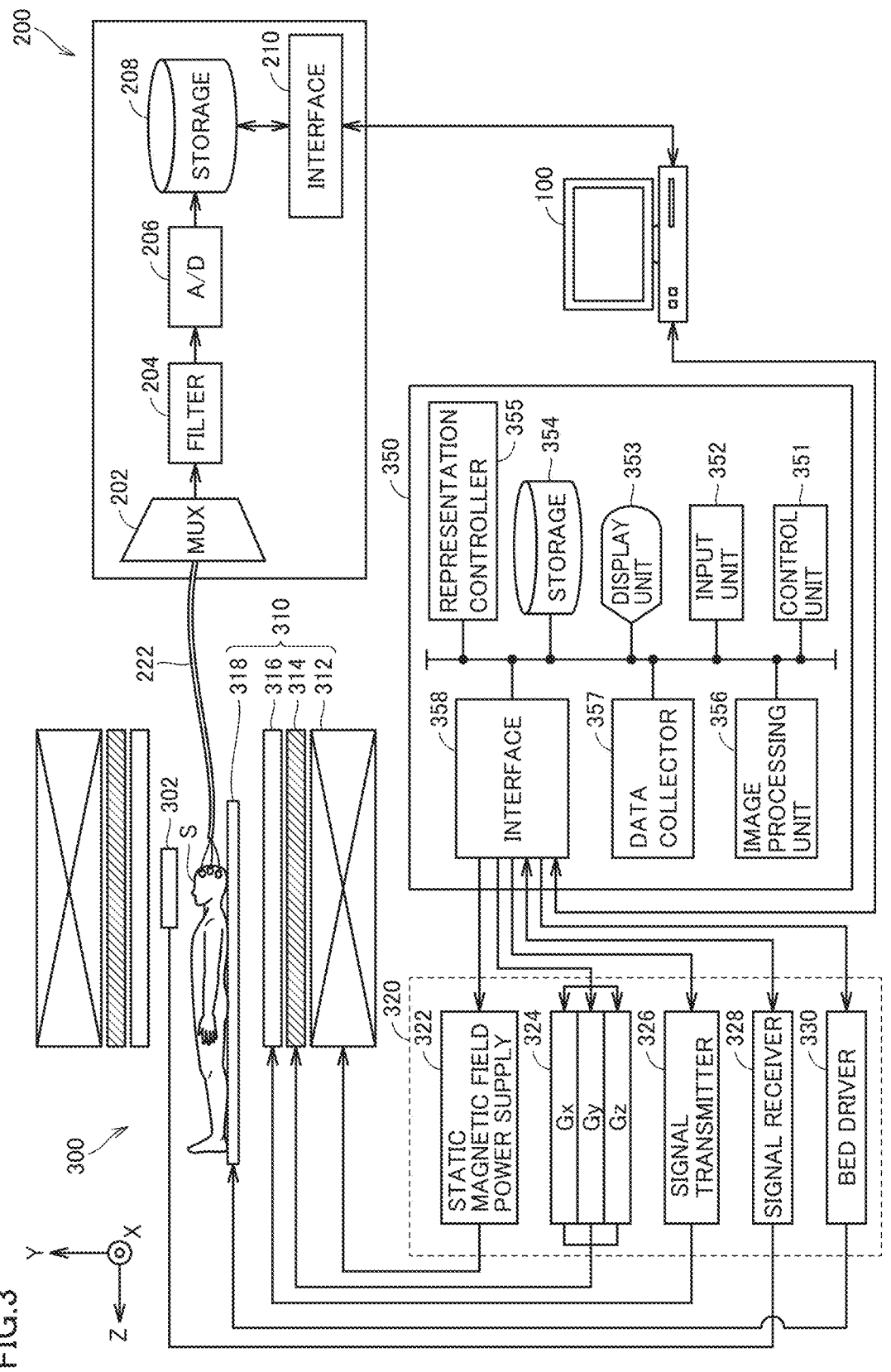
FIG. 3 is a schematic diagram showing an exemplary hardware configuration of an estimation system that estimates disorder-likelihood according to the present embodiment.

FIG. 3 is a schematic diagram showing an exemplary hardware configuration of estimation system 1 that estimates disorder-likelihood according to the present embodiment. Referring to FIG. 3, estimation system 1 includes a processing apparatus 100, an EEG apparatus 200, and an fMRI apparatus 300.

Processing apparatus 100 obtains brain wave measurement data (EEG measurement data) and measurement data (fMRI measurement data) of functional magnetic resonance imaging that are simultaneously measured from a subject. More specifically, processing apparatus 100 accepts EEG measurement data measured by EEG apparatus 200 and fMRI measurement data measured by fMRI apparatus 300 and determines an estimation model for estimating disorder-likelihood.

EEG apparatus 200 detects a signal (an electrical signal) representing brain waves generated in a plurality of sensors 220 arranged on the head of a subject S. EEG apparatus 200 includes a multiplexer 202, a noise filter 204, an analog to digital (A/D) converter 206, a storage 208, and an interface 210.

Multiplexer 202 sequentially selects one set of cables from among cables 222 connected to the plurality of sensors 220 and electrically connects the set of cables to noise filter 204. Noise filter 204 is a filter which removes noise, such as a high-frequency cut filter, and removes noise components contained in a signal (an electrical signal) representing brain waves generated in the set of cables corresponding to a selected channel.

A/D converter 206 samples an electrical signal (an analog signal) outputted from noise filter 204 every prescribed cycle and outputs the signal as a digital signal. Storage 208 successively stores chronological data (digital signals) outputted from A/D converter 206 in association with information representing a selected channel and timing (for example, time or a counter value).

Interface 210 outputs chronological data representing brain waves that is stored in storage 208 to processing apparatus 100 in response to an access from processing apparatus 100 or the like.

fMRI apparatus 300 measures brain activities by detecting electromagnetic waves generated by resonance from a specific nucleus (for example, a hydrogen nucleus) by applying high-frequency electromagnetic field at a resonant frequency to a region from which information on brain activities of subject S is to be obtained (which will also be referred to as a "region of interest" below).

fMRI apparatus 300 includes a magnetic field application mechanism 310, a reception coil 302, a driver 320, and a data processing unit 350.

Magnetic field application mechanism 310 applies controlled magnetic field (static magnetic field and gradient magnetic field) to a region of interest of subject S and emits radio frequency (RF) pulses thereto. More specifically, magnetic field application mechanism 310 includes a static magnetic field generation coil 312, a gradient magnetic field generation coil 314, an RF emitter 316, and a bed 318 including a bore in which subject S lies.

Driver 320 is connected to magnetic field application mechanism 310, and controls magnetic field applied to subject S and transmission and reception of RF pulse waves. More specifically, driver 320 includes a static magnetic field power supply 322, a gradient magnetic field power supply 324, a signal transmitter 326, a signal receiver 328, and a bed driver 330.

In FIG. 3 a central axis of a cylindrical bore in which subject S lies is defined as a Z axis and a horizontal direction and a vertical direction orthogonal to the Z axis are defined as an X axis and a Y axis, respectively.

Static magnetic field generation coil 312 generates static magnetic field in a Z-axis direction in the bore from a helical coil wound around the Z axis. Gradient magnetic field generation coil 314 includes an X coil, a Y coil, and a Z coil (none of which are shown) which generate gradient magnetic field in an X-axis direction, a Y-axis direction, and the Z-axis direction in the bore. RF emitter 316 emits RF pulses to a region of interest in subject S based on a high-frequency signal transmitted from signal transmitter 326 in accordance with a control sequence. Though FIG. 3 shows an exemplary configuration in which RF emitter 316 is contained in magnetic field application mechanism 310, RF emitter 316 may be provided on a side of bed 318, or RF emitter 316 and reception coil 302 may be integrated with each other.

Reception coil 302 receives electromagnetic waves (NMR signals) emitted from subject S and outputs an analog signal. The analog signal outputted from reception coil 302 is subjected to amplification and A/D conversion in signal receiver 328 and then output to data processing unit 350. Reception coil 302 is preferably arranged in proximity to subject S such that an NMR signal can be detected at high sensitivity.

Data processing unit 350 sets a control sequence for driver 320 and outputs a plurality of brain activity pattern images representing an activation factor of the brain as information representing brain activities, based on the NMR signal received by reception coil 302.

Data processing unit 350 includes a control unit 351, an input unit 352, a display unit 353, a storage 354, a representation controller 355, an image processing unit 356, a data collector 357, and an interface 358. Data processing unit 350 may be implemented by a dedicated computer or a general-purpose computer which performs prescribed processing by executing a control program stored in storage 354 or the like.

Control unit 351 controls an operation by each functional unit, such as generation of a control sequence for driving driver 320. Input unit 352 accepts various operations or information input from a not-shown operator. Display unit 353 has various images and various types of information relating to a region of interest in subject S shown on a screen. Storage 354 stores a control program for performing processing involved with fMRI, a parameter, image data (a three-dimensional model image or the like), and other electronic data. Image processing unit 356 generates a plurality of brain activity pattern images based on data of a detected NMR signal. Interface 358 exchanges various signals with driver 320. Data collector 357 collects data constituted of a set of NMR signals derived from a region of interest.

FIG. 4 is a schematic diagram showing an exemplary hardware configuration of processing apparatus 100 included in estimation system 1 that performs the estimation method according to the present embodiment. A computer in accordance with a general-purpose architecture can typically be adopted as processing apparatus 100. Referring to FIG. 4, processing apparatus 100 includes as its main components, a processor 102, a main storage 104, a control interface 106, a network interface 108, an input unit 110, a display unit 112, and a secondary storage 120.

Processor 102 is implemented by an operation processing circuit such as a central processing unit (CPU) or a graphical processing unit (GPU), and performs various functions which will be described later by executing codes included in various programs stored in secondary storage 120 in a designated order. Main storage 104 is implemented by a dynamic random access memory (DRAM) or the like and holds a code of a program executed by processor 102 or various types of work data necessary for execution of a program.

Processing apparatus 100 has a communication function, which is provided mainly by control interface 106 and network interface 108.

Control interface 106 exchanges data with data processing unit 350 of fMRI apparatus 300. Network interface 108 exchanges data with an external apparatus (for example, a data server apparatus on the cloud). Control interface 106 and network interface 108 are implemented by any communication component such as a wired local area network (LAN), a wireless LAN, a universal serial bus (USB), or Bluetooth®.

Input unit 110 is typically implemented by a mouse, a keyboard, or the like and accepts an operation by a user. Display unit 112 is typically implemented by a display and notifies a user of various types of information involved with a state of processing performed in processing apparatus 100 or an operation.

Secondary storage 120 is typically implemented by a hard disk or a solid state drive (SSD) and holds various programs executed by processor 102, various types of data necessary for processing, and a set value. More specifically, secondary storage 120 stores EEG measurement data 20, fMRI measurement data 30, an estimation model determination program 121, an estimation program 122, and an estimation model parameter 124.

C. Processing for Determining Estimation Model

Processing for determining an estimation model in the estimation method according to the present embodiment will now be described.

Figure 5:
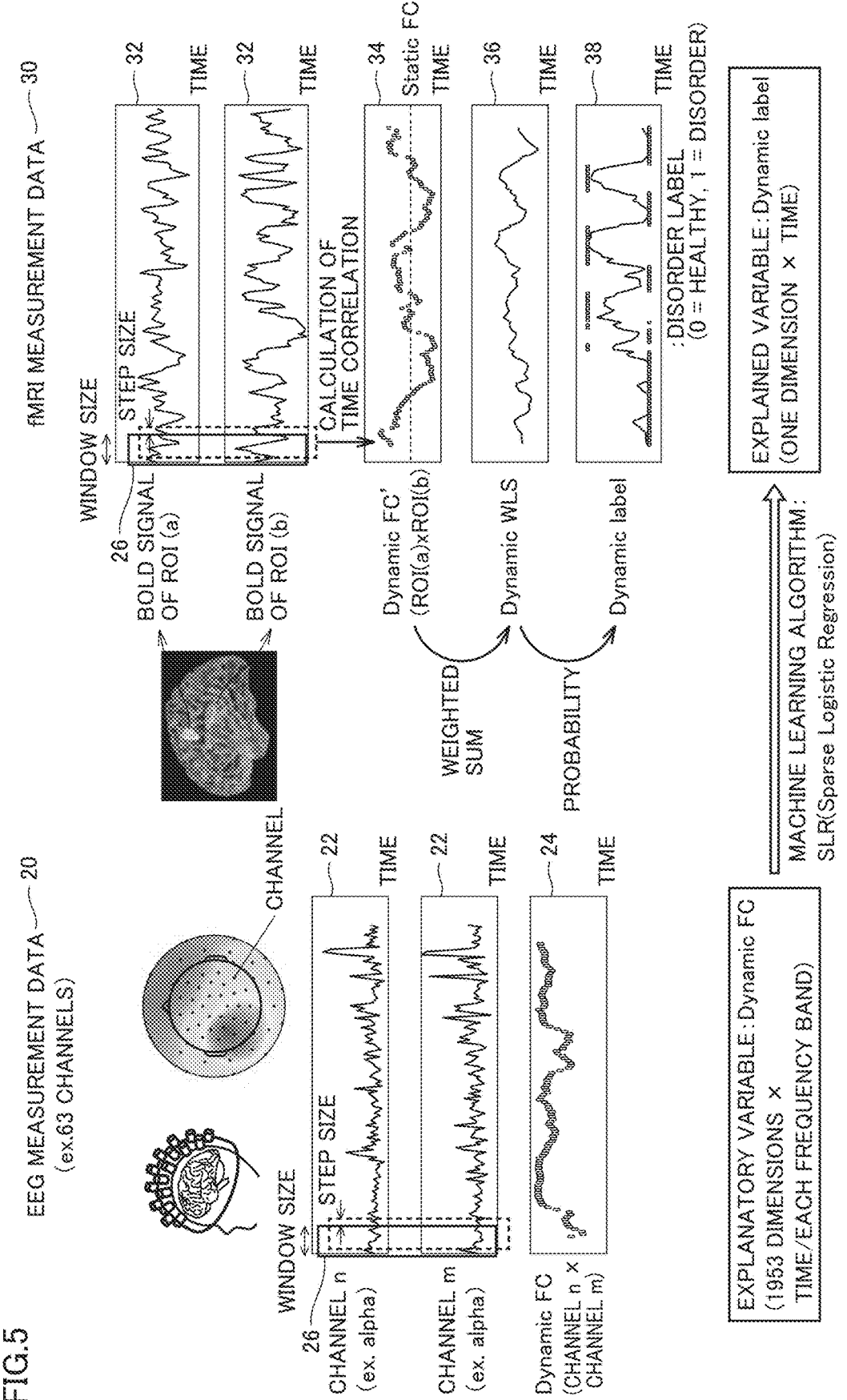
FIG. 5 is a diagram for illustrating processing for determining an estimation model in the estimation method according to the present embodiment.
Figure 6:
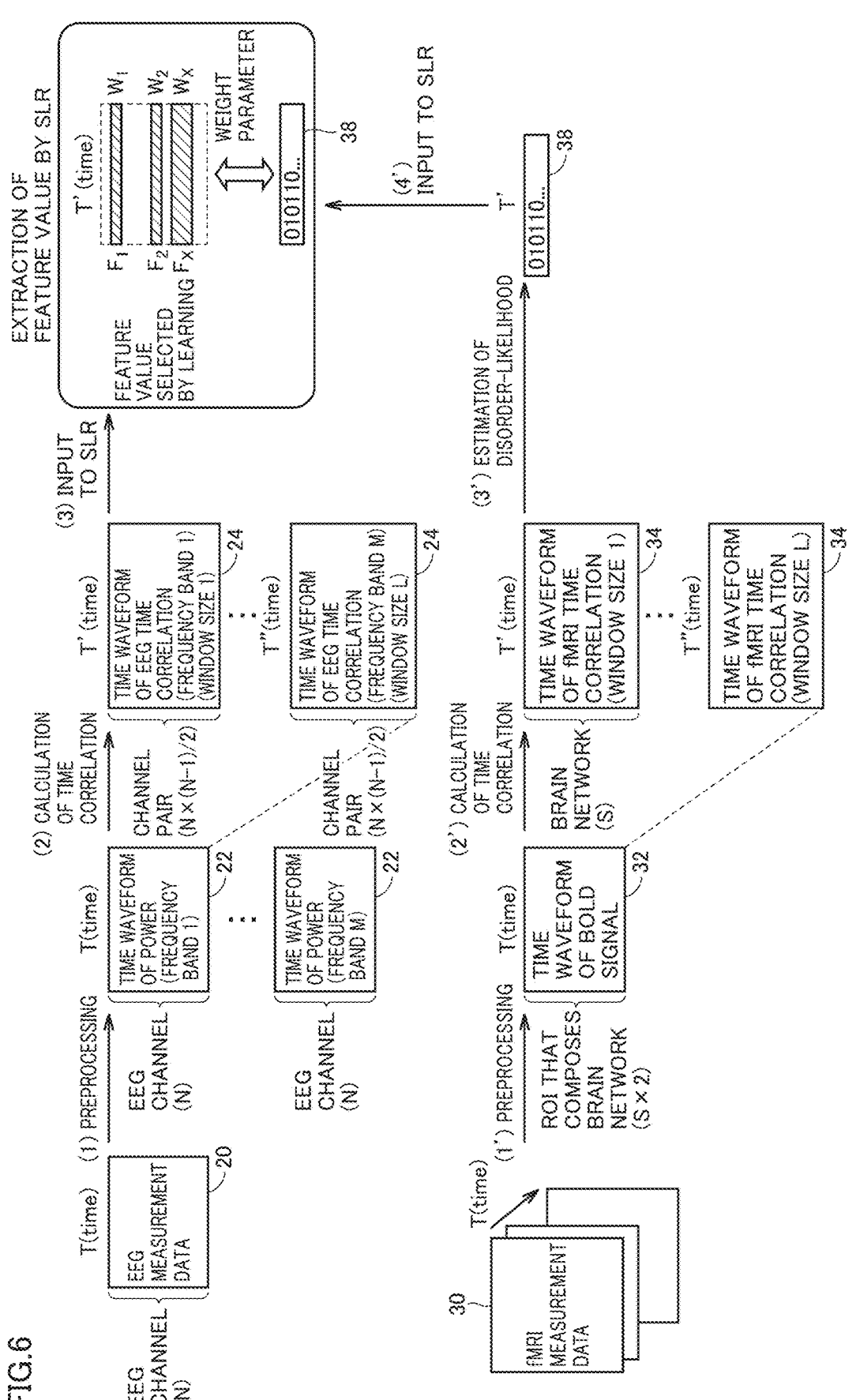
FIG. 6 is a diagram showing exemplary data processing for determining an estimation model in the estimation method according to the present embodiment.

FIG. 5 is a diagram for illustrating processing for determining an estimation model in the estimation method according to the present embodiment. FIG. 6 is a diagram showing exemplary data processing for determining an estimation model in the estimation method according to the present embodiment.

Processing for calculating FC which is an explanatory variable is performed on EEG measurement data 20 included in EEG/fMRI simultaneous measurement data and processing for calculating a disorder-likelihood label which is an explained variable is performed on fMRI measurement data 30 included in EEG/fMRI simultaneous measurement data. Such processing will be described with reference to FIGS. 5 and 6.

[c1: EEG Measurement Data 20)

EEG measurement data 20 is a collection of variations in signal (time waveforms) representing brain waves measured for each channel (sensor). EEG measurement data 20 is converted to a time waveform 22 of power for each frequency band by preprocessing (corresponding to (1) preprocessing in FIG. 6). Time waveform 22 of power means successive calculation for each unit time, of an average value of square values of amplitudes of corresponding frequency components included in EEG measurement data 20.

More specifically, in preprocessing, EEG measurement data 20 (time waveform) is subjected to frequency conversion to calculate an amplitude for each frequency. Then, one frequency or a plurality of frequencies included in a designated frequency band is/are selected, the amplitude(s) of the one selected frequency or the plurality of selected frequencies is/are squared, and an average value of the amplitude(s) is calculated. Power can thus be calculated.

When a sampling frequency of EEG measurement data 20 is high, down sampling to a prescribed sampling frequency may be performed and then frequency analysis may be conducted. For example, down sampling may be performed such that the sampling frequency is set to 1/TR [Hz] so as to correspond to an emission cycle (repetition time (TR)) of RF pulses in fMRI.

EEG measurement data 20 is thus preprocessed to generate time waveform 22 of power of N channels×M frequency bands. Examples of the frequency band include theta waves (θ waves: 5 to 8 Hz), alpha waves (α waves: 8 to 12

Hz), low beta waves (low β waves: 12 to 20 Hz), and high beta waves (high β waves: 20 to 30 Hz). For example, when the number of channels N is set to 63 and the number of frequency bands M is set to 4,252 (=63×4) time waveforms of power are generated.

Then, time correlation of time waveforms 22 of power between different channels for the same frequency band is calculated (corresponding to ((2) calculation of time correlation in FIG. 6).

"Time correlation" herein means a correlation value between time waveforms and a time waveform of a correlation value in a section included in a window 26 set in common for a plurality of time waveforms.

For EEG measurement data 20, time correlation between two time waveforms 22 of power is calculated. At this time, the time correlation means a time waveform of a correlation value with attention being paid to a temporal width of window 26 set for two time waveforms 22 of power. In other words, functional connectivity (FC) is calculated from the correlation value between time waveforms in the section included in window 26 set in common for time waveforms of brain waves in two channels of interest.

Window 26 has a prescribed window size (temporal width). A time waveform 24 of EEG time correlation can be calculated by sequentially shifting, by each step size, a setting position where window 26 is set (a temporal section from start time until end time) and by sequentially calculating correlation corresponding to each setting position of window 26. Calculated time waveform 24 of EEG time correlation corresponds to the FC.

Functional connectivity (FC) is thus calculated for each channel combination (each channel pair) based on correlation between channels included in EEG measurement data 20.

For example, when the number of channels N in EEG is set to 63, time waveform 24 of EEG time correlation can be calculated for each of 1953 (=N×(N−1)/2=63×(63−1)/2) channel combinations (channel pairs). Time waveform 24 of EEG time correlation has a time length corresponding to the number of times of shifting (the number of time steps) of window 26.

Time waveform 24 of EEG time correlation is calculated for each frequency band. In other words, time waveforms 24 of EEG time correlation for M frequency bands are generated.

Furthermore, with the window size (temporal width) of set window 26 being varied, time waveform 24 of EEG time correlation may be calculated for each of the windows.

Thus, time waveform 24 of EEG time correlation with three items of the channel pair, the frequency band, and the window size being varied may be employed as a feature value for estimating disorder-likelihood. In this case, time waveform 24 of EEG time correlation is outputted as a vector of channel combination (channel pair) dimensions× (the number of time steps corresponding to window 26) dimensions for each frequency band and/or for each window size.

Functional connectivity (FC) may thus be calculated for each frequency band included in EEG measurement data 20 and/or for each window size of set window 26.

A single vector for all frequency bands and all window sizes as being integrated may be generated. In this case, a vector of {(the number of channel combinations (channel pairs))×(the number of window sizes)×(the number of frequency bands)}dimensions×(the number of time steps) dimensions is outputted. In other words, in the example described above, a vector of 1953 dimensions×(the number of time steps) dimensions may be outputted for each frequency band and/or for each window size, or a vector of more dimensions resulting from integration of the above may be outputted.

(c2: fMRI Measurement Data 30)

fMRI measurement data 30 (that is, a brain activity pattern image) is an assembly of brain activity pattern images obtained for each emission cycle of RF pulses. It has already been known, to a brain activity in which region in the brain each of already known brain networks (resting state networks) corresponds. One region or a plurality of regions corresponding to each of such brain networks correspond(s) to region(s) of interest (which will also be abbreviated as an "ROI" below).

In the estimation method according to the present embodiment, an activity of each brain network is assumed to be defined by a combination of two ROIs.

Initially, fMRI measurement data 30 is subjected to preprocessing (corresponding to (1') preprocessing in FIG. 6) to calculate a BOLD signal 32 for each ROI. The BOLD signal means change over time in amount of activity dependent on a blood oxygen level for each ROI. More specifically, in preprocessing on fMRI measurement data 30, the BOLD signal is calculated based on an image feature value corresponding to the ROI included in a brain activity pattern image.

Then, time correlation of BOLD signal 32 between corresponding ROIs is calculated for each brain network (corresponding to (2') calculation of time correlation in FIG. 6). For fMRI measurement data 30, time correlation between two BOLD signals 32 is calculated. At this time, time correlation means a time waveform of a correlation value with attention being paid to a temporal width of window 26 set for two BOLD signals 32. In other words, functional connectivity (FC') is calculated from the correlation value between time waveforms in a section included in window 26 set in common for time waveforms representing the amounts of activity in two ROIs of interest.

Window 26 has a prescribed window size (temporal width). A time waveform 34 of BOLD time correlation can be calculated by sequentially shifting, by each step size, a setting position where window 26 is set (a temporal section from start time until end time) and by sequentially calculating correlation corresponding to each setting position of window 26. Time waveform 34 of BOLD time correlation represents change over time in correlation value and corresponds to functional connectivity (FC').

Time waveform 34 of BOLD time correlation can be calculated for each ROI combination, that is, for each brain network of interest. The functional connectivity (FC') is calculated for each brain network based on correlation between ROIs included in fMRI measurement data 30.

"Dynamic" in FIG. 5 means that a value is calculated for each window to which attention is paid, and "Static" means that a single value is calculated throughout a period. Therefore, "Static FC" in FIG. 5 means a correlation value over the entire period (single functional connectivity).

Disorder-likelihood is estimated based on thus calculated time waveform 34 (FC') of BOLD time correlation (corresponding to (3') estimation of disorder-likelihood in FIG. 6). It has been known from prior studies that disorder-likelihood is associated with a plurality of brain networks (that is, brain activities in a plurality of ROIs).

In the estimation method according to the present embodiment, with such advance information, WLS 36 which is a score representing disorder-likelihood to be estimated is calculated based on time waveforms 34 of BOLD time correlations corresponding to a plurality of brain networks associated with disorder-likelihood to be estimated. More specifically, WLS 36 is calculated by multiplying time waveforms 34 (FC') of a plurality of BOLD time correlations of interest by respective corresponding weight parameters and adding results of multiplication. Such a calculation method has been known as weighted linear summation (WLS).

WLS 36 which is a score representing disorder-likelihood is calculated based on the sum of results of multiplication of a plurality of functional connectivities (time waveforms 34 of BOLD time correlations) brought in correspondence with disorder-likelihood to be estimated by respective corresponding weight parameters.

A disorder-likelihood label 38 is calculated by thus calculating a score (WLS 36) representing disorder-likelihood to be estimated with the use of a plurality of time waveforms 34 (FC') of BOLD time correlations.

Furthermore, disorder-likelihood label 38 (label) is calculated by normalizing the score (WLS 36) representing disorder-likelihood and then subjecting the normalized score to threshold processing. When binarization processing is adopted as the threshold processing, disorder-likelihood label 38 is set to "0" meaning being healthy or "1" meaning disorder.

Disorder-likelihood label 38 is outputted as a vector of one dimension×(the number of set windows 26) dimension (s) that expresses disorder-likelihood to be estimated. Disorder-likelihood label 38 is handled as an explained variable. (c3: Processing for Determining Estimation Model)

The estimation model defines relation between time waveform 24 (FC) of EEG time correlation which is an explanatory variable and disorder-likelihood label 38 (label) which is an explained variable. In the estimation method according to the present embodiment, a feature value suitable for estimation of disorder-likelihood label 38 among feature values included in time waveform 24 of EEG time correlation which is expressed as a multi-dimensional vector is selected. In the estimation phase, disorder-likelihood is estimated based on information on the selected feature value (sequentially calculated time correlation). In other words, an estimation model for estimating disorder-likelihood is determined based on time waveform 24 (FC) of prescribed EEG time correlation by machine learning using time waveform 24 (FC) of EEG time correlation for each channel combination (for each channel pair) and disorder-likelihood label 38.

By thus making use only of at least one of feature values included in time waveform 24 of EEG time correlation which is an explanatory variable for estimation, dimensions can be compressed and reduced, so that an amount of computation involved with estimation can be reduced and estimation processing can be faster.

Though any machine learning algorithm can be employed for determination of the estimation model, by way of example, sparse logistic regression (SLR) may be adopted.

Specifically, time waveform 24 of EEG time correlation is inputted as an explanatory variable to the SLR which is a machine learning algorithm (corresponding to (3) input to SLR in FIG. 6) and disorder-likelihood label 38 is inputted as an explained variable to the SLR which is the machine learning algorithm (corresponding to (4') input to SLR in FIG. 6). Then, a feature value suitable for estimation of disorder-likelihood label 38 is selected by machine learning.

Figure 7:
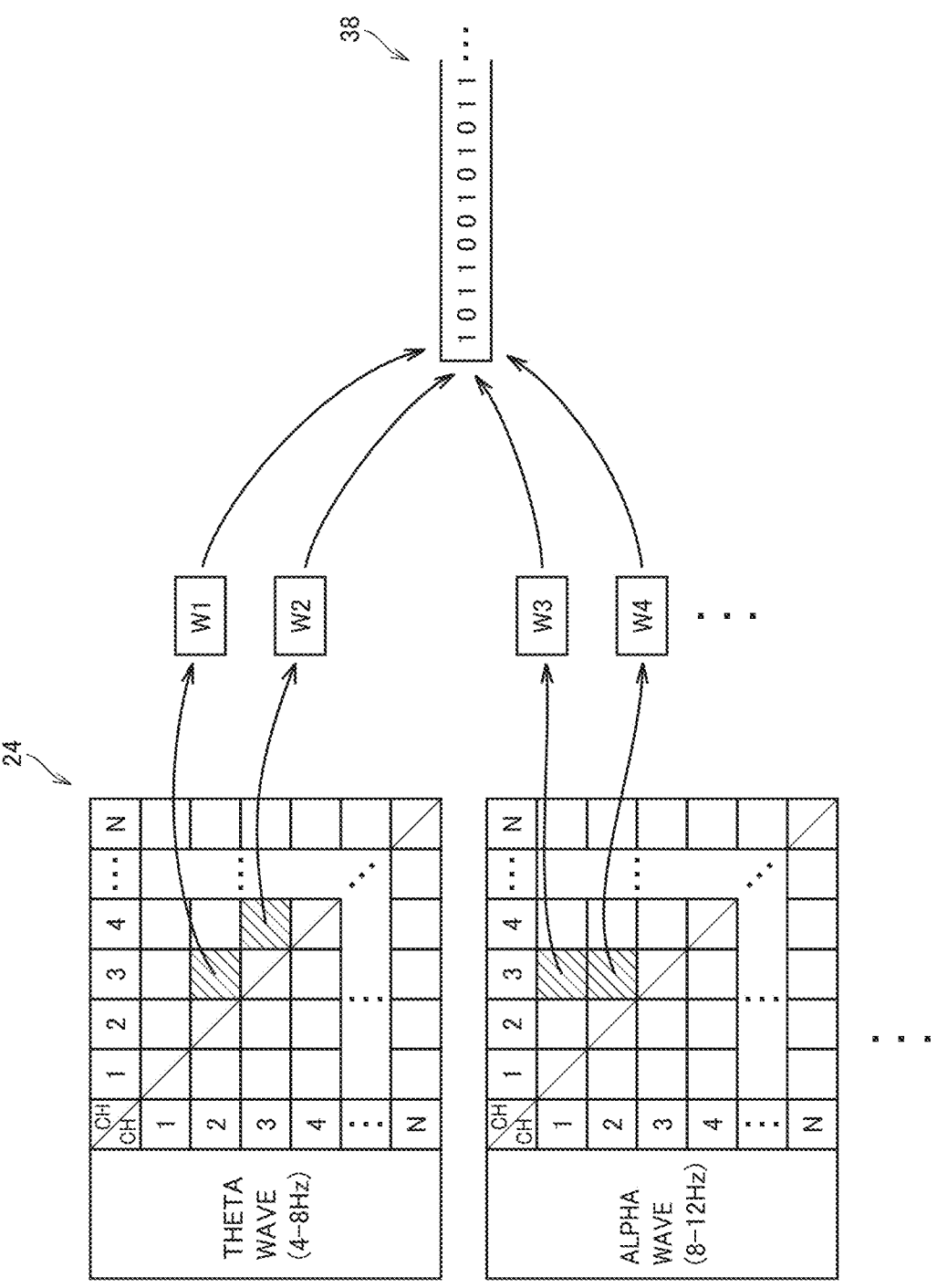
FIG. 7 is a diagram for illustrating overview of an estimation model determined in the estimation method according to the present embodiment.

FIG. 7 is a diagram for illustrating overview of an estimation model determined in the estimation method according to the present embodiment. Referring to FIG. 7, time waveform 24 of EEG time correlation exhibits a group of feature values in accordance with the number of channels in EEG for each frequency band. Though not shown, time waveform 24 of EEG time correlation is calculated also for each window size.

A prescribed number of (for example, thirty) feature values $F_i$ (i=1, 2, . . . , x) suitable for estimation of disorder-likelihood label 38 among a large number of feature values that constitute a multi-dimensional vector of time waveform 24 of EEG time correlation are selected by machine learning.

Furthermore, a weight parameter $W_i$ (i=1, 2, . . . , x) may be determined for each of selected feature values. For example, a larger value of weight parameter $W_i$ may be set for feature value $F_i$ more suitable for estimation of disorder-likelihood label 38.

Alternatively, instead of a technique to select a feature value and determine weight parameter $W_i$ corresponding to selected feature value $F_i$, only weight parameter $W_i$ may be determined. For example, by setting weight parameter $W_i$ to zero for a feature value not used for estimation of disorder-likelihood label 38, a result as in an example where a feature value is not selected can be obtained.

Thus, the determined estimation model includes information for selecting time waveform 24 (feature value $F_i$) of EEG time correlation to be used for estimation among time waveforms 24 (FC) of EEG time correlation for each channel combination (for each channel pair) and weight parameter $W_i$ brought in correspondence with selected time waveform 24 of EEG time correlation.

In the estimation phase, disorder-likelihood of a subject is sequentially estimated only based on EEG measurement data 20 with the use of the feature value and the corresponding weight parameter determined in a procedure as described above.

(c4: Processing Procedure)

FIG. 8 is a flowchart showing a processing procedure in the estimation method according to the present embodiment. Some steps shown in FIG. 8 may be performed by execution of a program in processing apparatus 100.

Referring to FIG. 8, initially, EEG measurement data 20 and fMRI measurement data 30 are obtained by simultaneous measurement of EEG and fMRI (step S100). In other words, processing apparatus 100 obtains measurement data (EEG measurement data 20) of brain waves and measurement data (fMRI measurement data 30) of fMRI simultaneously measured from a subject.

Processing apparatus 100 preprocesses obtained EEG measurement data 20 to calculate a time waveform of power for each frequency band (step S102). Then, processing apparatus 100 calculates a time waveform of EEG time correlation for each window size based on the calculated time waveform of power (step S104). In other words, processing apparatus 100 calculates functional connectivity (FC) for each channel combination based on correlation between channels included in EEG measurement data 20.

In parallel to processing in steps S102 and S104 or after step S104, processing apparatus 100 preprocesses obtained fMRI measurement data 30 to calculate a time waveform of a BOLD signal for each ROI that composes a brain network (step S112). Then, processing apparatus 100 calculates a time waveform of BOLD time correlation for each window size based on the calculated time waveform of the BOLD signal (step S114). In other words, processing apparatus 100 calculates functional connectivity (FC') for each brain network based on correlation between ROIs included in fMRI measurement data 30.

Then, processing apparatus 100 selects a time waveform of BOLD time correlation in accordance with disorder-likelihood to be estimated among calculated time waveforms of BOLD time correlations, multiplies the time waveform with each corresponding weight parameter, and adds results of multiplication to calculate WLS (step S116). Then, processing apparatus 100 calculates the disorder-likelihood label representing disorder-likelihood by normalizing the calculated WLS and then binarizing the normalized WLS (step S118). In other words, processing apparatus 100 calculates the disorder-likelihood label by calculating a score (WLS) representing disorder-likelihood to be estimated based on a plurality of functional connectivities (FC').

Finally, processing apparatus 100 determines the feature value and the weight parameter for estimating the disorder-likelihood label by machine learning using the time waveform of EEG time correlation and the disorder-likelihood label (step S120). In other words, processing apparatus 100 determines the estimation model for estimating disorder-likelihood based on the prescribed functional connectivity (FC) by machine learning using the functional connectivity (FC) and the disorder-likelihood label for each channel combination.

The estimation model can be determined through such a procedure.

D. EEG/fMRI Simultaneous Measurement

"(1) EEG/fMRI simultaneous measurement" shown in FIG. 1 and step S100 shown in FIG. 8 will now be described. With estimation system 1 shown in FIG. 3, subject S with a sensor being attached to the head is laid in a bore of fMRI apparatus 300, and EEG and fMRI are performed in parallel.

Processing apparatus 100 stores measurement data from EEG apparatus 200 and fMRI apparatus 300 in correspondence with each other, with common time being defined as the reference. EEG measurement data 20 and fMRI measurement data 30 common in time axis can be obtained based on correspondence of measurement data based on such common time.

E. Calculation of Functional Connectivity (FC) from EEG Measurement Data 20

"(2) Calculate functional connectivity (FC)" shown in FIG. 1 and steps S102 to S104 shown in FIG. 8 will now be described in detail.

As preprocessing on EEG measurement data 20 (time waveform), initially, a time waveform is subjected to frequency conversion. For example, fast Fourier transform or the like can be employed as processing for frequency conversion. Without being limited to fast Fourier transform, Hilbert transform or discrete Fourier transform may be employed.

For preprocessing in step S102 in FIG. 8, by frequency conversion of EEG measurement data 20, data on a frequency domain (relation between a frequency and an amplitude) is calculated. By calculating for each frequency band of interest, an average value of square values of amplitudes of frequencies included in the frequency band, power of the frequency band is calculated.

In step S104 in FIG. 8, any two channels are selected and the window is sequentially shifted along a time axis, so that a correlation value between time waveforms of power within the window is sequentially calculated.

Through such processing, time waveform 24 (FC) of EEG time correlation can be calculated.

Figure 9:
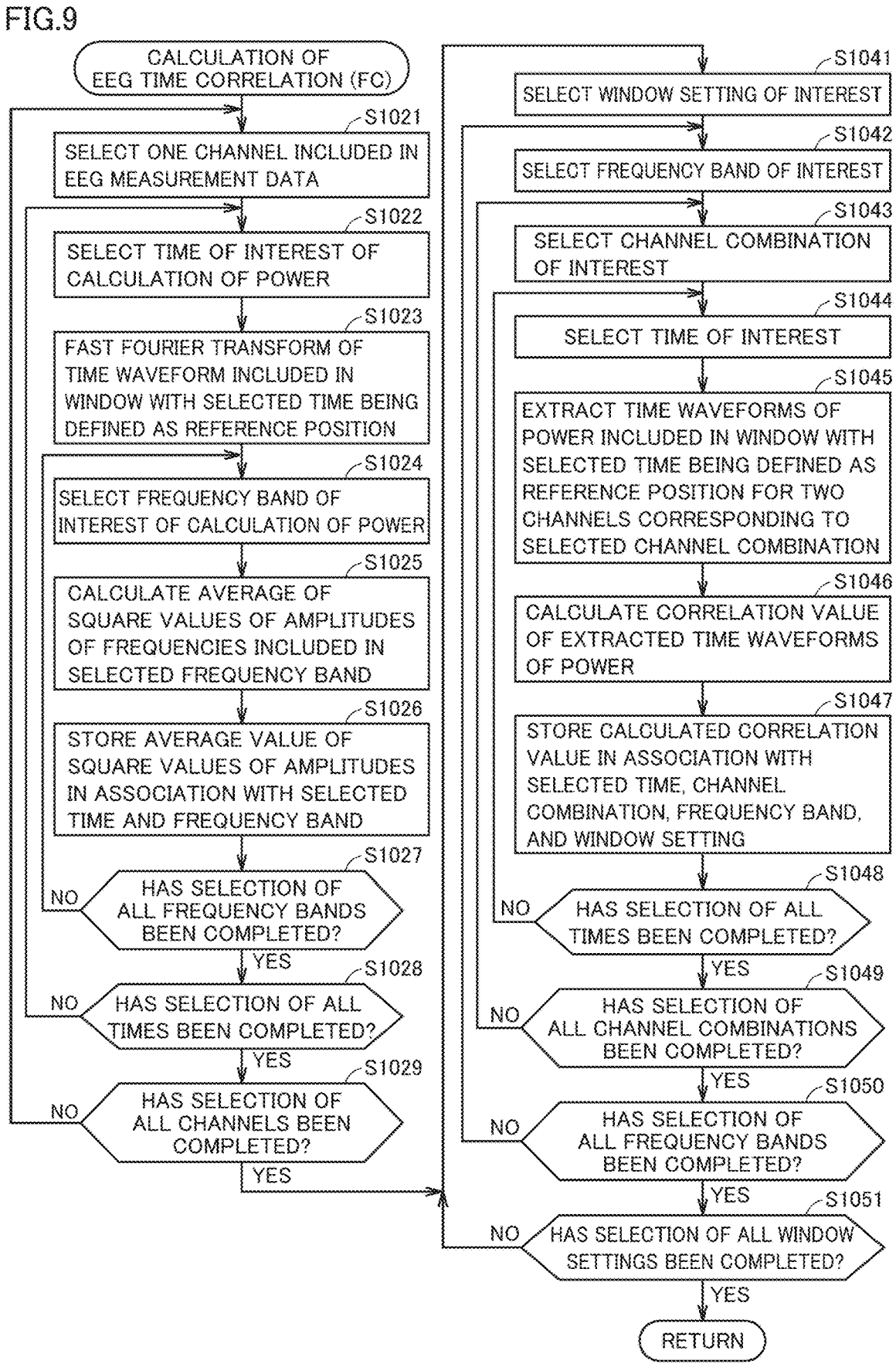
FIG. 9 is a flowchart showing a more detailed processing procedure in steps S102 and S104 in FIG. 8.

FIG. 9 is a flowchart showing a more detailed processing procedure in steps S102 and S104 in FIG. 8. Referring to FIG. 9, processing apparatus 100 selects one channel included in obtained EEG measurement data 20 (step S1021), selects time of interest of calculation of power (step S1022), and subjects a time waveform included in the window with the selected time being defined as a reference position to fast Fourier transform (step S1023).

The time waveform included in the window may be subjected to moving average along the time axis and then to fast Fourier transform. By application of such moving average, a noise component at a high frequency can be reduced.

Then, processing apparatus 100 selects a frequency band of interest of calculation of power (step S1024) and calculates an average value of square values of amplitudes of frequencies included in the selected frequency band (step S1025). Then, processing apparatus 100 has the average value of the square values of the amplitudes stored in association with the selected time and the selected frequency band (step S1026).

Processing apparatus 100 determines whether or not selection of all frequency bands has been completed (step S1027). When selection of all frequency bands has not been completed (NO in step S1027), processing in step S1024 or later is repeated.

When selection of all frequency bands has been completed (YES in step S1027), processing apparatus 100 determines whether or not selection of all times has been completed (step S1028). When selection of all times has not been completed (NO in step S1028), processing in step S1022 or later is repeated.

When selection of all times has been completed (YES in step S1028), processing apparatus 100 determines whether or not selection of all channels has been completed (step S1029). When selection of all channels has not been completed (NO in step S1029), processing in step S1021 or later is repeated.

When selection of all channels has been completed (YES in step S1029), at this stage, processing for calculating time waveform 22 of power for each frequency band is completed. Then, processing for calculating time waveform 24 (FC) of EEG time correlation follows.

Processing apparatus 100 selects window setting (the window size and the step size) of interest of calculation of EEG time correlation (step S1041) and selects a frequency band of interest of calculation of EEG time correlation (step S1042).

For window setting (the window size and the step size), a plurality of combinations may be prepared in advance or only one type of window setting may be prepared.

Processing apparatus 100 selects a channel combination of interest of calculation of EEG time correlation (step S1043).

Then, processing apparatus 100 selects time of interest of calculation of EEG time correlation (step S1044), extracts time waveforms of power included in the window with the selected time being defined as the reference position for two channels corresponding to the selected channel combination (step S1045), and calculates a correlation value of the extracted time waveforms of power (step S1046). Then, processing apparatus 100 has the calculated correlation value stored in association with the selected time, channel combination, frequency band, and window setting (step S1047).

Processing apparatus 100 determines whether or not selection of all times has been completed (step S1048).

When selection of all times has not been completed (NO in step S1048), processing in step S1044 or later is repeated.

When selection of all times has been completed (YES in step S1048), processing apparatus 100 determines whether or not selection of all channel combinations has been completed (step S1049). When selection of all channel combinations has not been completed (NO in step S1049), processing in step S1043 or later is repeated.

When selection of all channel combinations has been completed (YES in step S1049), processing apparatus 100 determines whether or not selection of all frequency bands has been completed (step S1050). When selection of all frequency bands has not been completed (NO in step S1050), processing in step S1042 or later is repeated.

When selection of all frequency bands has been completed (YES in step S1050), processing apparatus 100 determines whether or not selection of all window settings has been completed (step S1051). When selection of all window settings has not been completed (NO in step S1051), processing in step S1041 or later is repeated.

When selection of all window settings has been completed (YES in step S1051), at this stage, processing for calculating time waveform 24 (FC) of EEG time correlation is completed.

F. Processing for Estimating Disorder-Likelihood from fMRI Measurement Data 30

"(3) Estimate disorder-likelihood based on a plurality of brain networks" shown in FIG. 1 and steps S112 to S118 shown in FIG. 8 will now be described in detail.

Initially, in preprocessing (step S112) on fMRI measurement data 30 (brain activity pattern image), BOLD signal 32 for each ROI is calculated from the brain activity pattern image. In extraction of this BOLD signal 32, processing for compensating for delay in time caused in fMRI is performed.

More specifically, transform y(t) into a BOLD signal representing an amount of activity for each ROI corresponds to addition of an error e(t) to convolution of s(t) and h(t) as shown in an expression (1) below, where s(t) represents BOLD signal 32 representing a neural state of the ROI to which attention is paid and h(t) represents a hemodynamic response function (HRF).

$$y(t)=s(t)\otimes h(t)+e(t) \tag{1}$$

HRF(t) is dependent on emission cycle TR of RF pulses in fMRI.

An estimated value $\hat{s}(t)$ of the neural state can be expressed as in an expression (2) below, with the use of a Wiener filter d(t).

$$\tilde{s}(t)=d(t)\otimes y(t) \tag{2}$$

With H(x), Y(x), E(x), and D(x) being defined as results of Fourier transform of h(t), y(t), e(t), and d(t), estimated value $\hat{s}(t)$ of the neural state can be expressed as in an expression (3) below.

$$\tilde{s}(t) = FT^{-1}(D(\omega)Y(\omega)) = FT^{-1}\left(\frac{H^{*}(\omega)Y(\omega)}{|H(\omega)|^{2} + |E(\omega)|^{2}}\right) \tag{3}$$

Estimated value s(t) of the neural state shown in the expression (3) above corresponds to the BOLD signal. In other words, estimated value s(t) of the neural state is estimated by deconvolution of observed y(t) with HRF. By deconvolution with HRF, delay in time (displacement between measurement points) between EEG measurement data 20 and fMRI measurement data 30 is compensated for.

Figure 10:
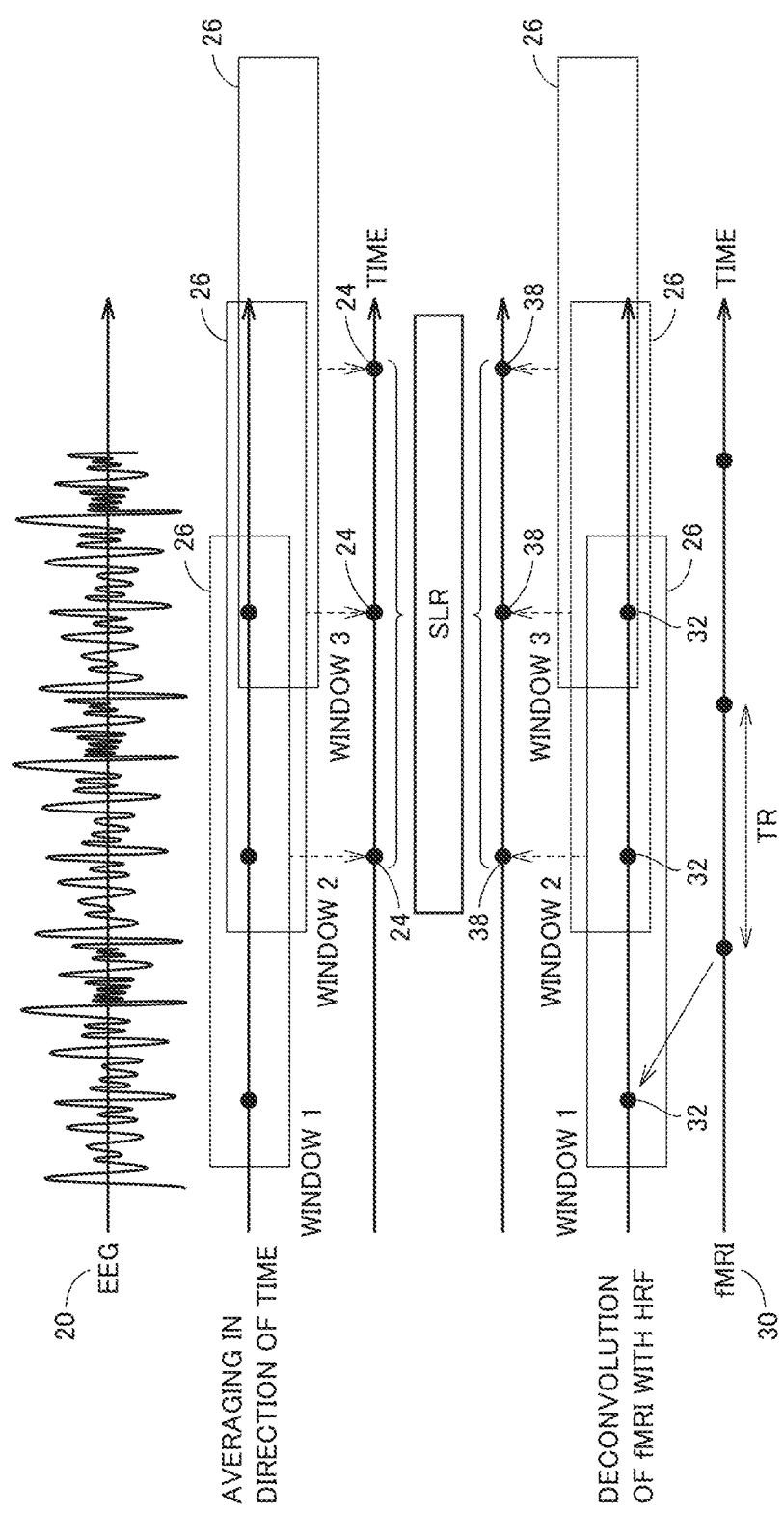
FIG. 10 is a diagram for illustrating overview of preprocessing on EEG measurement data and fMRI measurement data.

FIG. 10 is a diagram for illustrating overview of preprocessing on EEG measurement data 20 and fMRI measurement data 30.

Referring to FIG. 10, window 26 is set for EEG measurement data 20 by being sequentially shifted by each step size, and time waveform 24 of EEG time correlation can be calculated by calculating EEG time correlation for each window 26.

For fMRI measurement data 30, deconvolution with HRF compensates for delay in time involved with emission of RF pulses and then BOLD signal 32 is calculated. In other words, by deconvolution with HRF, the time axis of EEG measurement data 20 and the time axis of BOLD signal 32 can substantially match with each other. Then, disorder-likelihood label 38 is calculated based on BOLD signal 32.

In step S114 in FIG. 8, for each combination of two ROIs, the window is sequentially shifted along the time axis and a correlation value between time waveforms of the BOLD signals within the window is sequentially calculated. The combination of two ROIs may be a combination of identical ROIs.

In steps S116 and S118 in FIG. 8, time waveforms of a plurality of BOLD time correlations in accordance with disorder-likelihood to be estimated are multiplied with respective corresponding weight parameters, and results of multiplication are added to calculate WLS. Furthermore, by normalizing and binarizing the calculated WLS, the disorder-likelihood label representing disorder-likelihood is calculated. More specifically, WLS 36 can be calculated as in an expression (4) shown below, based on time waveform 34 (FC'(k)) of kth BOLD time correlation and a corresponding weight parameter $W_{FC}(k)$.

$$WLS=\Sigma FC'(k)\times W_{FC}(k) \tag{4}$$

WLS is a score which represents a larger numeric value as a degree of disorder-likelihood is higher, with 0 being defined as a boundary. WLS can be normalized to a probability p in accordance with an expression (5) shown below.

$$p=1/(1+\exp(-WLS)) \tag{5}$$

Probability p (0≤p≤1) is closer to 1 as the degree of disorder-likelihood is higher, with 0.5 being defined as a boundary.

In accordance with the disorder-likelihood to be estimated, functional connectivity (FC') of interest is selected. For example, NPL 3 discloses a disorder discriminator for schizophrenia (SCZ) with the use of sixteen functional connectivities (FC'). NPL 4 discloses a disorder discriminator for melancholic major depressive disorder (MDD) with the use of ten functional connectivities (FC').

By referring to such prior art, in accordance with disorder-likelihood to be estimated, a plurality of functional connectivities (FC') are selected, and WLS can be determined by calculating the sum of values obtained by multiplication of the plurality of functional connectivities by respective weight parameters $W_{FC}$ brought in correspondence with selected functional connectivities (FC').

By finally binarizing probability p, the disorder-likelihood label can be calculated.

FIG. 11 is a flowchart showing a more detailed processing procedure in steps S112 to S118 shown in FIG. 8. Referring to FIG. 11, processing apparatus 100 selects an ROI of interest of calculation of a BOLD signal (step S1121) and extracts each amount of activity from an image feature value in a region corresponding to the ROI selected from fMRI measurement data 30 (step S1122). By deconvolution of change over time in extracted amount of activity with HRF, a time waveform of the BOLD signal is calculated (step S1123) and the time waveform is stored in association with the selected ROI (step S1124).

Processing apparatus 100 determines whether or not selection of all ROIs has been completed (step S1125). When selection of all ROIs has not been completed (NO in step S1125), processing in step S1121 or later is repeated.

When selection of all ROIs has been completed (YES in step S1125), at this stage, processing for calculating a BOLD signal for each ROI is completed. Then, processing for calculating time waveform 34 of BOLD time correlation follows.

Processing apparatus 100 selects an ROI combination of interest of calculation of BOLD time correlation (step S1141).

Then, processing apparatus 100 selects time of interest of calculation of BOLD time correlation (step S1142), extracts time waveforms of BOLD signals 32 included in a window with the selected time being defined as the reference position for two ROIs corresponding to the selected ROI combination (step S1143), and calculates a correlation value of the extracted time waveforms of the BOLD signals (step S1144). Then, processing apparatus 100 has the calculated correlation value stored in association with the selected time and ROI combination (step S1145).

Processing apparatus 100 determines whether or not selection of all times has been completed (step S1146). When selection of all times has not been completed (NO in step S1146), processing in step S1142 or later is repeated.

When selection of all times has been completed (YES in step S1146), processing apparatus 100 determines whether or not selection of all ROI combinations has been completed (step S1147). When selection of all ROI combinations has not been completed (NO in step S1147), processing in step S1141 or later is repeated.

When selection of all ROI combinations has been completed (YES in step S1147), at this stage, processing for calculating time waveform 34 of BOLD time correlation is completed. Then, processing for calculating WLS follows.

Processing apparatus 100 selects disorder-likelihood to be estimated (step S1161) and determines a plurality of brain networks (ROI combination) associated with selected disorder-likelihood (step S1162). Processing apparatus 100 determines weight parameters corresponding to respective ones of the plurality of determined brain networks (step S1163). Then, processing apparatus 100 multiplies time waveforms 34 of BOLD time correlations of the plurality of determined brain networks by respective corresponding weight parameters and calculates the sum of results of multiplication (step S1164). The calculated sum is adopted as WLS corresponding to the disorder-likelihood to be estimated.

Processing apparatus 100 determines whether or not selection of all disorder-likelihoods has been completed (step S1165). When selection of all disorder-likelihoods has not been completed (NO in step S1165), processing in step S1161 or later is repeated.

When selection of all disorder-likelihoods has been completed (YES in step S1165), at this stage, processing for calculating WLS for each disorder-likelihood is completed. Then, processing for calculating the disorder-likelihood label follows.

The processing apparatus calculates probability p by normalizing calculated WLS (step S1181) and outputs a string of a value 0 or 1 by subjecting calculated probability p to threshold processing (step S1182). The outputted string of the value 0 or 1 serves as the disorder-likelihood label representing disorder-likelihood.

G. Modeling Processing

"(4) Determine estimation model" shown in FIG. 1 and step S120 shown in FIG. 8 will now be described in detail.

In processing for determining an estimation model, machine learning of relation between time waveform 24 (FC) of EEG time correlation which is an explanatory variable and disorder-likelihood label 38 which is an explained variable is carried out to determine a prescribed number of (for example, thirty) feature values suitable for estimation of disorder-likelihood label 38 among a large number of feature values that compose a multi-dimensional vector included in time waveform 24 of EEG time correlation and corresponding weight parameters.

Though any machine learning algorithm can be employed as a technique for such machine learning, an example in which SLR is adopted will be described by way of example. A specific processing procedure in SLR will be described below.

An expression (6) shown below is assumed as a linear discriminant function for discrimination of two classes $S_1$ and $S_2$ based on a weighted sum of feature values.

$$f(x;\theta) = \Sigma_{d=1}^{D} \theta_d x_d + \theta_0 \tag{6}$$

In the expression, x represents a feature value ($x=(x_1, x_2, \ldots, x_D)^t \in R^D$) within a D-dimensional space and $\theta$ represents a weight vector ($\theta=(\theta_1, \theta_2, \ldots, \theta_D)^t$) including a bias term. A hyperplane corresponding to $f(x; \theta)=0$ defines a boundary between class $S_1$ and class $S_2$.

In SLR, possibility that each feature value belongs to class $S_2$ on the hyperplane that defines the boundary between class $S_1$ and class $S_2$ is computed with the use of a logistic function as shown in an expression (7).

$$p = \frac{1}{1 + \exp(-f(x;\theta))} \equiv P(S_2 \mid x) \tag{7}$$

In the expression, probability p has a value within a range from 0 to 1, and the probability attains to 0 when a condition of $f(x; \theta)=0$ is satisfied (being on the hyperplane) and exhibits 1 when $f(x; \theta)=0$ is located at a positive or negative infinite point (a position distant from the hyperplane). In other words, probability p means possibility that any feature value x belongs to class $S_2$.

By introduction of any binary output variable y (y=0 corresponds to class $S_1$ and y=1 corresponds to class $S_2$), a probability function as shown in an expression (8) below can be defined for a data string $\{(x_1, y_1), (x_2, y_2), \ldots, (x_N, y_N)\}$ including N input-output elements.

$$P(y_1, \ldots, y_N \mid x_1, \ldots, x_N; \theta) = \prod_{n=1}^{N} P(y_n \mid x_n; \theta) = \prod_{n=1}^{N} p_n^{y_n} (1 - p_n)^{1-y_n} \tag{8}$$

$$p_n \equiv P(y_n = 1 \mid x_n; \theta) = \frac{1}{1 + \exp(-f(x_n; \theta))} \tag{9}$$

Since each term in the expression (8) expresses a probability $p_n$ of an nth sample ($p_n$ when $y_n=1$ and $1-p_n$ when $y_n=0$) (see an expression (9)), a product of the terms shown in the expression (8) means the probability of all samples included in the data string.

Machine learning aims at introduction of a probability function $l(\theta)$ as shown in an expression (10) and search for a weight vector $\theta$ that maximizes a value of probability function $l(\theta)$ defined in the expression (10).

$$l(\theta)=\Sigma_{n=1}^{N}[y_n \log p_n + (1-y_n)\log(1-p_n)] \qquad (10)$$

Probability function $l(\theta)$ includes probability $p_n$ of a non-linear element dependent on weight vector $\theta$. Therefore, for solving probability function $l(\theta)$, a gradient and a Hessian matrix can be used. When weight vector $\theta$ $(=(\theta_1, \theta_2, \ldots, \theta_D)^t)$ that maximizes probability function $l(\theta)$ can be determined, at least one of feature values can be selected as the feature value suitable for estimation based on a value of an element (weight parameter) included in weight vector $\theta$.

For example, a prescribed number of (for example, thirty) weight parameters are selected in a descending order of magnitude, and feature values corresponding to the selected weight parameters are selected.

The feature value (designation of a channel pair, a frequency band, and a window size to be used in EEG time correlation) and the corresponding weight parameter to be used for estimation of disorder-likelihood label 38 can thus be determined.

Figure 12:
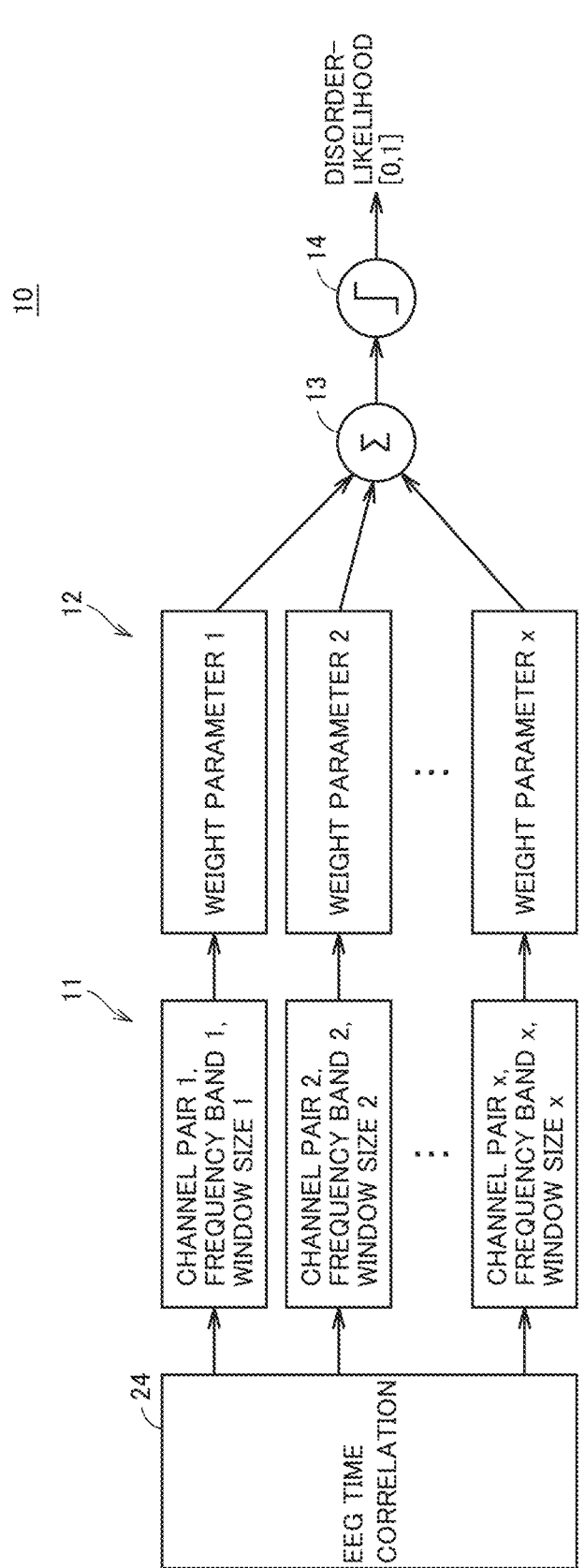
FIG. 12 is a diagram for illustrating overview of the determined estimation model.

FIG. 12 is a diagram for illustrating overview of the determined estimation model. Referring to FIG. 12, in the estimation phase, time waveform 24 of EEG time correlation is inputted to estimation model 10. More specifically, an amount of information on a prescribed window size (for example, thirty seconds) is inputted for each step size (for example, thirty seconds).

Estimation model 10 includes a plurality of combinations of feature value information 11 and a weight parameter 12. Only information corresponding to feature value information 11 (EEG time correlation selected as the feature value) included in estimation model 10 in inputted time waveform 24 of EEG time correlation is used. Then, the used EEG time correlation is multiplied by corresponding weight parameter 12, a sum of results thereof is calculated by an adder 13, and the sum is binarized to 0 or 1 by a binarizer 14. A result of binarization is outputted as disorder-likelihood.

Though the channel pair, the frequency band, and the window size are each defined as a variable factor in determination of the estimation model, the frequency band and the window size may be determined in advance as a feature value condition.

More specifically, in determining a feature value condition (the frequency band and the window size), EEG/fMRI simultaneous measurement data is obtained in a plurality of sessions and a frequency band and a window size highest in discrimination performance (for example, an indicator shown with area under the curve (AUC)) may be determined by such a technique as cross validation. By thus determining the feature value condition in advance, an amount of computation necessary for processing for determining the estimation model can be reduced.

The frequency band and/or the window size included in EEG measurement data 20 to be inputted to the estimation model may thus be determined in advance depending on a subject.

H. Estimation Phase

Exemplary processing in the estimation phase using the estimation model determined in the processing in the learning phase as described above will now be described.

In the estimation phase, EEG measurement data measured from the subject is inputted to the estimation model to estimate disorder-likelihood of the subject. Neurofeedback training represents a typical application of such an estimation phase.

Figure 13:
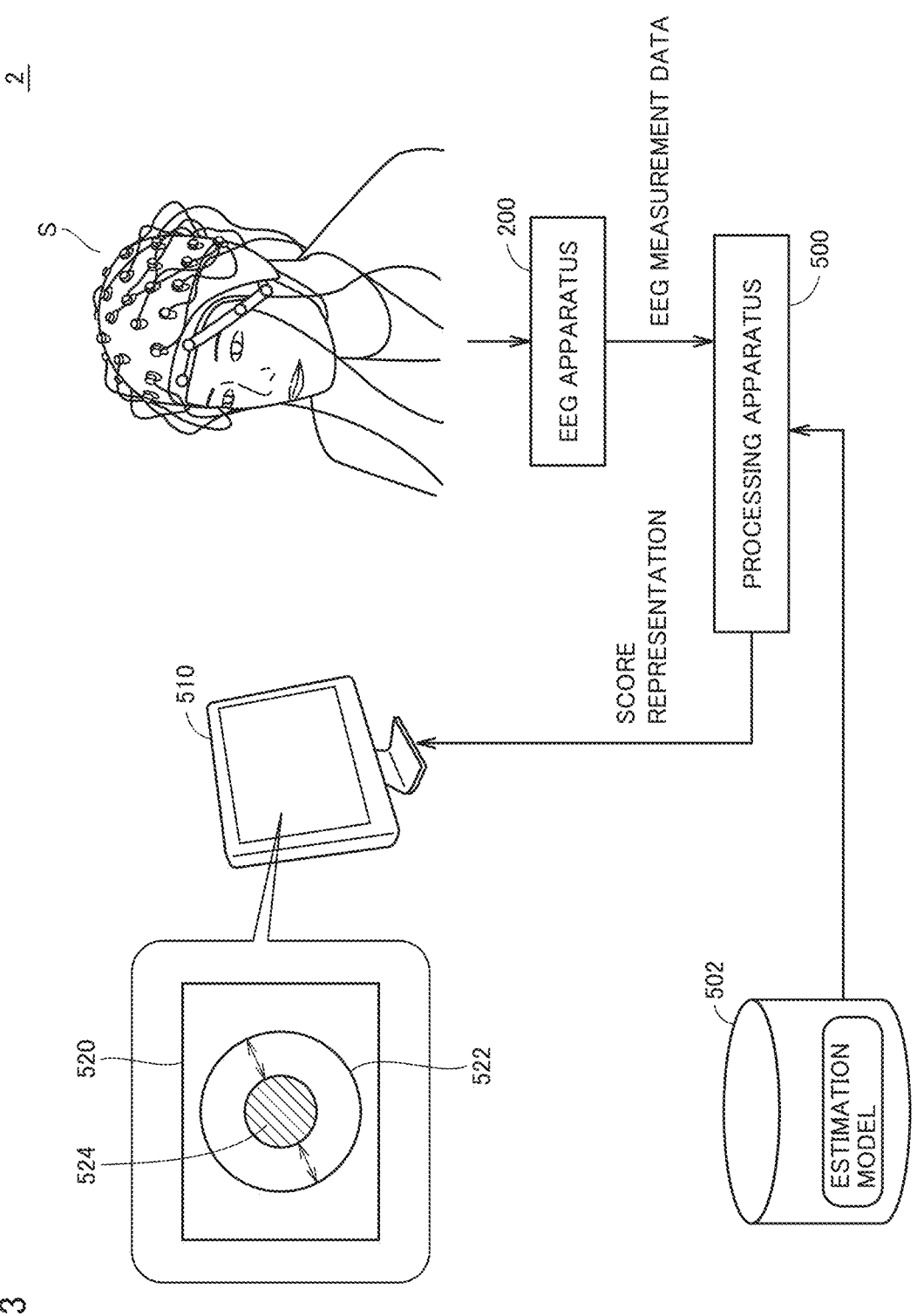
FIG. 13 is a diagram for illustrating overview of neurofeedback training by making use of the estimation method according to the present embodiment.

FIG. 13 is a diagram for illustrating overview of neurofeedback training using the estimation method according to the present embodiment. Referring to FIG. 13, a brain activity training apparatus 2 for conducting neurofeedback training includes an EEG apparatus 200, a storage device 502, a display device 510, and a processing apparatus 500.

An estimation model is stored in storage device 502. The estimation model stored in storage device 502 is generated before neurofeedback training is conducted. Storage device 502 may be implemented by a storage included in processing apparatus 500 or a server apparatus 400 shown in FIG. 14.

Display device 510 represents an exemplary presentation apparatus and provides visual and/or aural information to a user.

EEG apparatus 200 corresponds to an electroencephalograph and measures measurement data of brain waves of subject S in neurofeedback training. Measurement data of brain waves measured by EEG apparatus 200 includes a time waveform for a plurality of channels corresponding to respective ones of a plurality of sensors arranged in a head of subject S, as in EEG apparatus 200 shown in FIG. 1. In other words, since substantially the same EEG apparatus 200 is used in generation of the estimation model and in neurofeedback training, EEG measurement data included in EEG/fMRI simultaneous measurement data used in generation of the estimation model includes a time waveform for each channel corresponding to each channel of EEG measurement data measured in neurofeedback training.

Processing apparatus 500 obtains EEG measurement data by EEG from subject S and estimates disorder-likelihood with the estimation model determined in advance. Disorder-likelihood is estimated every cycle (typically, every step size). Processing apparatus 500 calculates a score in accordance with the estimated disorder-likelihood and provides a score representation 520 in accordance with the calculated score on display device 510. Processing apparatus 500 thus calculates the score in accordance with disorder-likelihood of subject S with the estimation model based on measurement data from EEG apparatus 200 and presents information in accordance with the calculated score to the subject. In other words, processing apparatus 500 outputs a signal for representation corresponding to disorder-likelihood to display device 510.

Processing apparatus 500 may be implemented by execution of a brain activity training program by a general-purpose computer.

For example, score representation 520 includes a reference circle 522 and a score circle 524 varied in size in accordance with the score. In accordance with disorder-likelihood estimated based on EEG measurement data measured from subject S, the size of score circle 524 is sequentially updated.

Subject S is informed in advance of the fact that the subject is rewarded as score circle 524 is close to reference circle 522 or score circle 524 deviates from reference circle 522. Subject S is more conscious of use of the brain for calculation, association, meditation, or the like such that the size of score circle 524 moves in a designated direction on the user's own will or in response to an external instruction. As subject S is more conscious of use of the brain, aimed alleviation or treatment of a disorder can be achieved.

In neurofeedback training where the estimation method according to the present embodiment is made use of, disorder-likelihood can be estimated at any location so long as estimation model 10 and EEG measurement data 20 are available. With the use of such an advantage, for example, EEG and fMRI are simultaneously conducted once with the use of a dedicated facility and thereafter neurofeedback training can be performed at any location.

Figure 14:
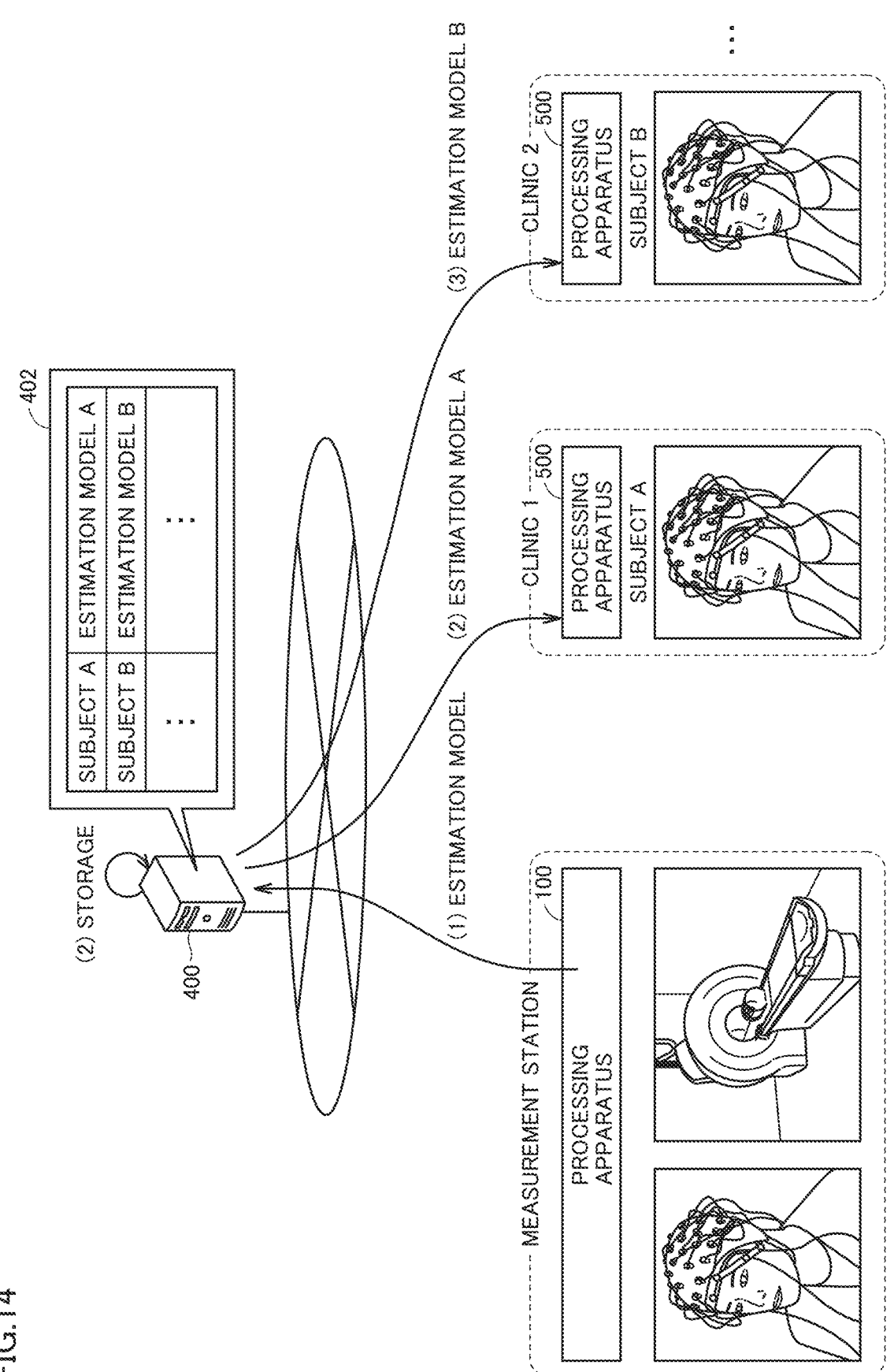
FIG. 14 is a schematic diagram showing an implementation of the estimation method according to the present embodiment.

FIG. 14 is a schematic diagram showing an implementation of the estimation method according to the present embodiment. Referring to FIG. 14, for example, at a dedicated measurement station, EEG and fMRI of each subject are simultaneously measured, and processing apparatus 100 determines estimation model 10 for each subject. Determined estimation model 10 is transmitted from the measurement station to server apparatus 400.

Subject data 402 including the estimation model for each subject is held in server apparatus 400.

Not only the measurement station but also a clinic desired by each subject of one or more clinics accesses server apparatus 400 to obtain the estimation model corresponding to each subject. At each clinic, processing apparatus 500 as will be described later is arranged and neurofeedback training as shown in FIG. 13 is conducted based on the obtained estimation model.

Cost for conducting neurofeedback training can be reduced with the use of a system as shown in FIG. 14.

I. Functional Configuration

An exemplary functional configuration of an apparatus included in estimation system 1 that realizes the estimation method according to the present embodiment will now be described.

(i1: Processing Apparatus 100)

Figure 15:
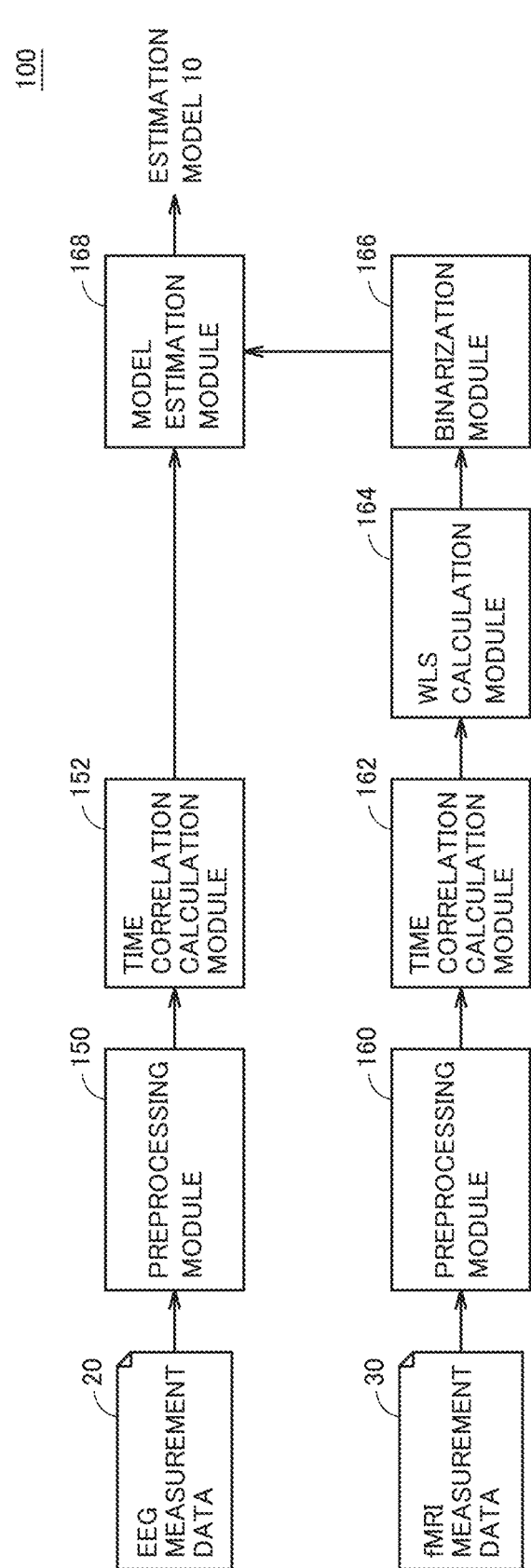
FIG. 15 is a schematic diagram showing an exemplary functional configuration of a processing apparatus in the estimation system according to the present embodiment.

FIG. 15 is a schematic diagram showing an exemplary functional configuration of processing apparatus 100 in estimation system 1 according to the present embodiment. Each function shown in FIG. 15 is typically performed by execution of an estimation model determination program by processor 102 of processing apparatus 100.

Estimation model determination program 121 may be executed by one processor or a plurality of processors included in processing apparatus 100 or by a plurality of processing apparatuses in coordination with one another. In the latter example, a plurality of computers arranged on a network, or what is called a cloud system, may be used. Furthermore, instead of a configuration implemented by execution of a program by the processor (software implementation), the entirety or a part thereof may be implemented by a hard-wired configuration such as a field-programmable gate array (FPGA) or an application specific integrated circuit (ASIC).

Each program according to the present embodiment may be mounted in such a form as utilizing a function provided by an operating system (OS), and such an example may also be encompassed in the technical scope of the invention of the present application.

Referring to FIG. 15, processing apparatus 100 includes preprocessing modules 150 and 160, time correlation calculation modules 152 and 162, a WLS calculation module 164, a binarization module 166, and a model estimation module 168.

Preprocessing module 150 converts EEG measurement data 20 into time waveform 22 of power. Time waveform 22 of power may be calculated for each frequency band and/or window size.

Time correlation calculation module 152 calculates time waveform 24 of EEG time correlation from time waveform 22 of power for each of channel combinations (channel pairs).

Preprocessing module 160 calculates BOLD signal 32 for each ROI from fMRI measurement data 30.

Time correlation calculation module 162 calculates time waveform 34 (FC') of BOLD time correlation from BOLD signal 32 for each ROI.

WLS calculation module 164 calculates WLS 36 which is a score representing disorder-likelihood to be estimated, based on time waveforms 34 of BOLD time correlations corresponding to a plurality of brain networks associated with disorder-likelihood to be estimated.

Binarization module 166 calculates disorder-likelihood label 38 (label) which represents a result of normalization of WLS 36 and binarization of disorder-likelihood.

Model estimation module 168 determines a feature value and a weight parameter for estimating disorder-likelihood label 38 based on time waveform 24 of EEG time correlation and disorder-likelihood label 38. A set of determined feature value and weight parameter is outputted as estimation model 10.

(i2: Processing Apparatus 500)

An exemplary functional configuration implemented in processing apparatus 500 shown in FIGS. 13 and 14 will now be described. Since processing apparatus 500 is similar in hardware configuration to processing apparatus 100 shown in FIG. 4 described above, detailed description will not be repeated.

Figure 16:
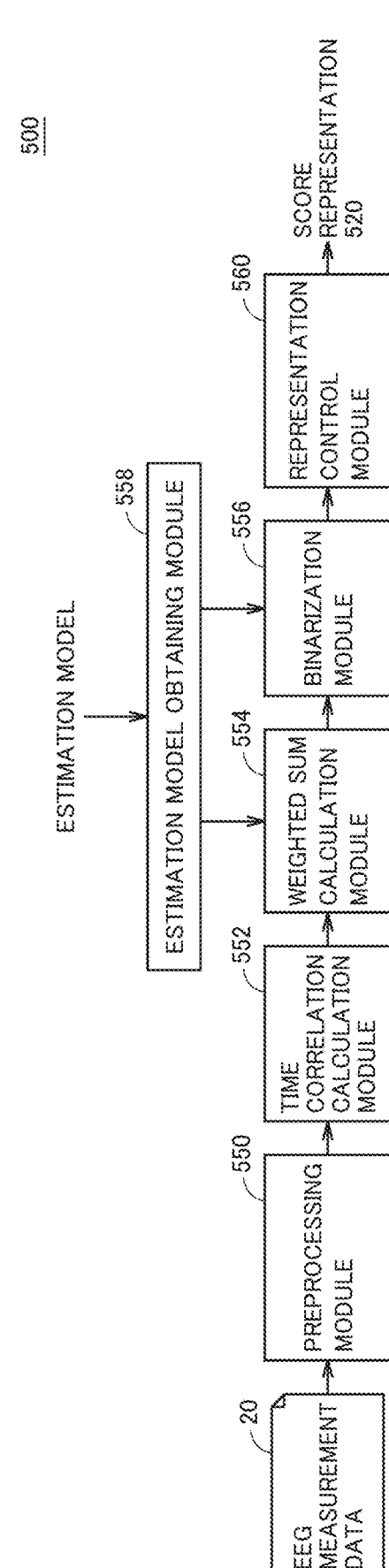
FIG. 16 is a schematic diagram showing an exemplary functional configuration of a processing apparatus in the estimation system according to the present embodiment.

FIG. 16 is a schematic diagram showing an exemplary functional configuration of processing apparatus 500 in estimation system 1 according to the present embodiment. Each function shown in FIG. 16 is performed by execution of an estimation program (similar to estimation program 122 shown in FIG. 4) by the processor of processing apparatus 500.

The estimation program may be executed by one or more processors in processing apparatus 500 or by a plurality of processing apparatuses in coordination with one another. In the latter example, a plurality of computers arranged on a network, or what is called a cloud system, may be used. Furthermore, instead of a configuration implemented by execution of a program by the processor (software implementation), the entirety or a part thereof may be implemented by a hard-wired configuration such as an FPGA or an ASIC.

Each program according to the present embodiment may be mounted in such a form as utilizing a function provided by an OS, and such an example may also be encompassed in the technical scope of the invention of the present application.

Referring to FIG. 16, processing apparatus 500 includes a preprocessing module 550, a time correlation calculation module 552, a weighted sum calculation module 554, a binarization module 556, an estimation model obtaining module 558, and a representation control module 560.

Preprocessing module 550 converts EEG measurement data 20 into time waveform 22 of power. Time waveform 22 of power may be calculated for each frequency band and/or window size.

Time correlation calculation module 552 calculates time waveform 24 of EEG time correlation from time waveform 22 of power for each of channel combinations (channel pairs).

Estimation model obtaining module 558 obtains estimation model 10 corresponding to a subject from server apparatus 400 or the like. Estimation model 10 includes a set of a feature value and a weight parameter for estimating disorder-likelihood label 38.

Weighted sum calculation module 554 selects one feature value or a plurality of feature values (EEG time correlation(s)) of interest in time waveforms 24 of EEG time correlations in accordance with estimation model 10 obtained by estimation model obtaining module 558 and calculates as WLS 36, the sum of values obtained by multiplication of feature value(s) by respective corresponding weight parameter(s).

Binarization module 556 calculates disorder-likelihood (0 or 1) which represents a result of normalization of WLS 36 and binarization of disorder-likelihood.

Representation control module 560 calculates a score based on a value of disorder-likelihood sequentially outputted from binarization module 556 and calculates score representation 520 for representation on display device 510. Change in symptom of the subject is thus assessed based on the score in accordance with the estimated disorder-likelihood of the subject.

J. Example

Some of results obtained by application of the estimation method according to the present embodiment to actual subjects will now be described.

In examples which will be described below, a healthy person or a subject determined as being subclinical was defined as a target. Being subclinical means a state determined to highly likely to exhibit at least one symptom of a disorder of interest based on contents of answers to questions for assessing a degree of the symptom.

(j1: Feature Value Condition)

An exemplary result of assessment of accuracy in estimation of a feature value condition for determining an estimation model will initially be described.

Each subject was simultaneously subjected to EEG and fMRI in a resting state to obtain EEG/fMRI simultaneous measurement data. EEG/fMRI simultaneous measurement data in at least eight sessions (equal to or shorter than five minutes per session) was obtained for each subject. Two disorders of interest, that is, schizophrenia (SCZ) (see NPL 3) and depression (MDD) (see NPL 4), were assumed.

Of obtained EEG/fMRI simultaneous measurement data in eight sessions, EEG/fMRI simultaneous measurement data in seven sessions was used to determine the estimation model and EEG/fMRI simultaneous measurement data in one remaining session was used as validation data, to thereby assess estimation performance by leave one out cross validation (LOOCV). Mean AUC was employed as an indicator for assessment of estimation performance.

Figure 17:
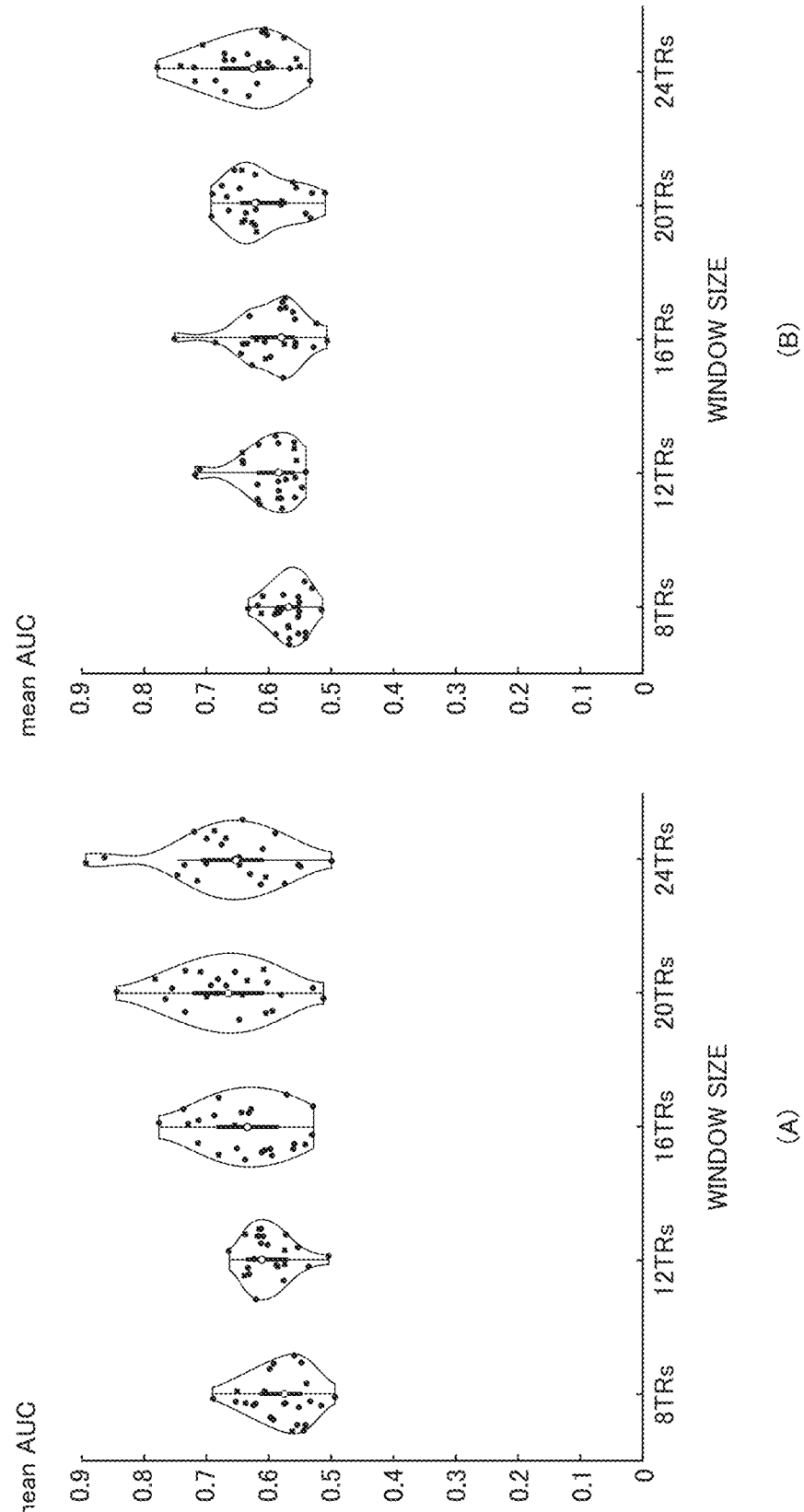
FIG. 17 is a diagram showing an exemplary result of assessment of a feature value condition in the estimation method according to the present embodiment.

FIG. 17 is a diagram showing an exemplary result of assessment of a feature value condition in the estimation method according to the present embodiment. FIG. 17 shows variation in estimation performance with variation in window size in calculation of time correlation (8 TR, 12 TR, 16 TR, 20 TR, and 24 TR). TR represents an emission cycle of RF pulses.

FIG. 17 (A) shows an exemplary result of assessment when schizophrenia (SCZ) was defined as the disorder of interest and FIG. 17 (B) shows an exemplary result of assessment when depression (MDD) was defined as the disorder of interest.

As shown in FIGS. 17 (A) and (B), with variation in window size, an average value of the mean AUC and a degree of variation thereof were also varied.

As shown in FIG. 17 (A), regarding schizophrenia (SCZ), it can be seen that the overall average of the mean AUC was good when the window size as the feature value condition was set to 20 TR. When the window size was set to 24 TR, however, some of subjects exhibited the highest mean AUC.

As shown in FIG. 17 (B), regarding depression (MDD), variation was less than variation in the case of schizophrenia (SCZ). Regarding depression (MDD), it can be seen that the overall average of the mean AUC was good when the window size as the feature value condition was set to 20 TR or 24 TR.

As shown in FIG. 17, it can be seen that selection of an optimal feature value condition for each subject is preferred.

(j2: Specificity Depending on Target of Estimation Model)

Specificity depending on target of the estimation model will now be described.

FIG. 17 described above shows the result of assessment of performance in estimation of the score representing disorder-likelihood of schizophrenia (SCZ) for the estimation model determined from EEG measurement data in connection with schizophrenia (SCZ) (which will also be referred to as a "schizophrenia estimation model" below) and the result of assessment of performance in estimation of the score representing disorder-likelihood of depression (MDD) for the estimation model determined from EEG measurement data in connection with depression (MDD) (which will also be referred to as a "depression estimation model" below). An exemplary result of cross assessment of these models is shown below.

Figure 18:
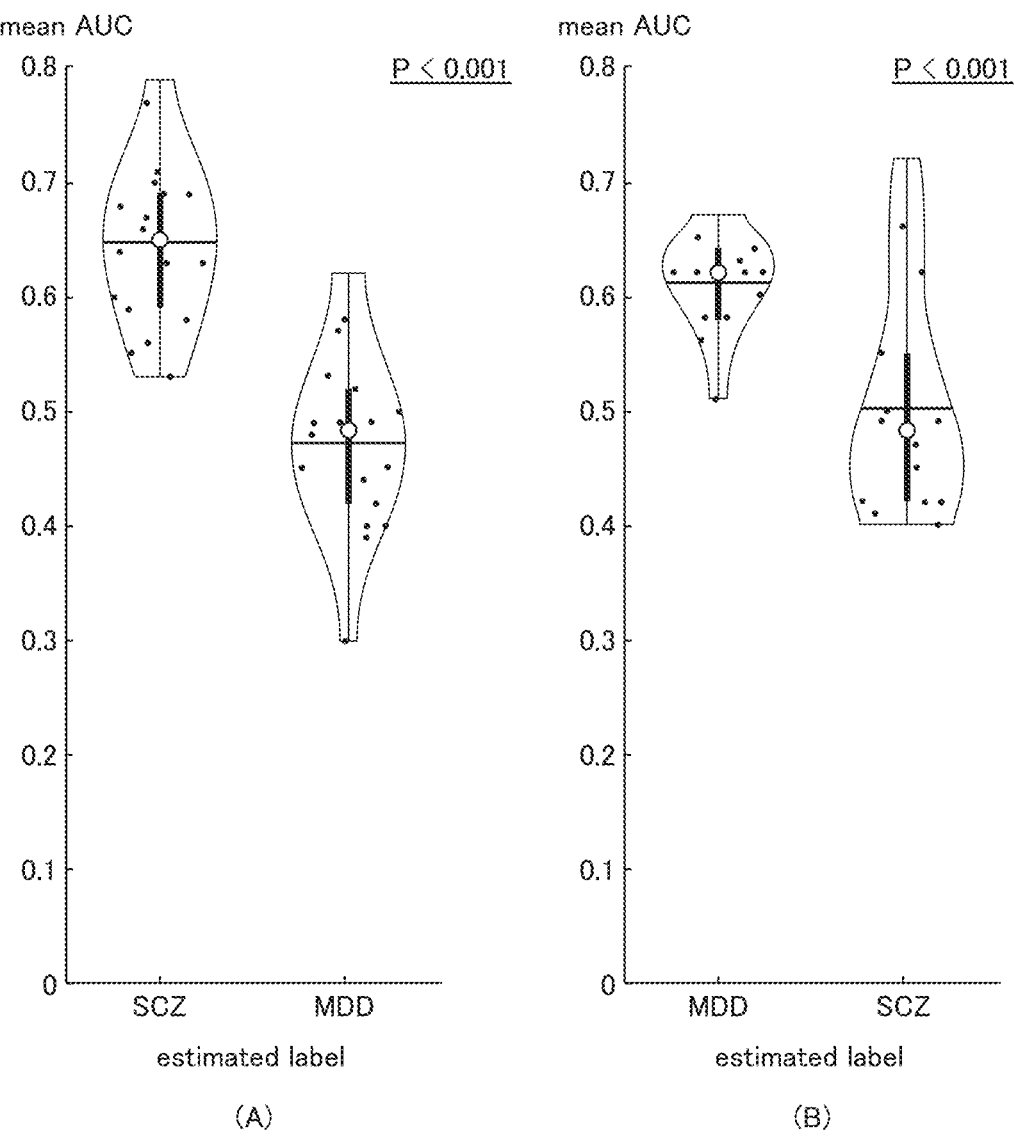
FIG. 18 is a diagram showing an exemplary result of assessment of specificity depending on target of the estimation model determined by the estimation method according to the present embodiment.

FIG. 18 is a diagram showing an exemplary result of assessment of specificity depending on target of the estimation model determined by the estimation method according to the present embodiment.

FIG. 18 (A) shows estimation performance (mean AUC) in estimation of disorder-likelihood of schizophrenia (SCZ) and estimation performance in estimation of disorder-likelihood of depression (MDD) with the use of the schizophrenia estimation model. FIG. 18 (B) shows estimation performance in estimation of disorder-likelihood of depression (MDD) and estimation performance in estimation of disorder-likelihood of schizophrenia (SCZ) with the use of the depression estimation model.

As shown in FIG. 18 (A), the schizophrenia estimation model exhibits estimation performance specific for estimation of disorder-likelihood of schizophrenia (SCZ). As shown in FIG. 18 (B), on the other hand, the depression estimation model exhibits estimation performance specific for estimation of disorder-likelihood of depression (MDD).

According to the result of cross validation of accuracy in estimation of disorder-likelihood shown in FIGS. 18 (A) and (B), it can be seen that the estimation model determined by the estimation method according to the present embodiment is target specific.

(j3: Neurofeedback Training)

Exemplary neurofeedback training with the estimation model determined by the estimation method according to the present embodiment will now be described.

Figure 19:
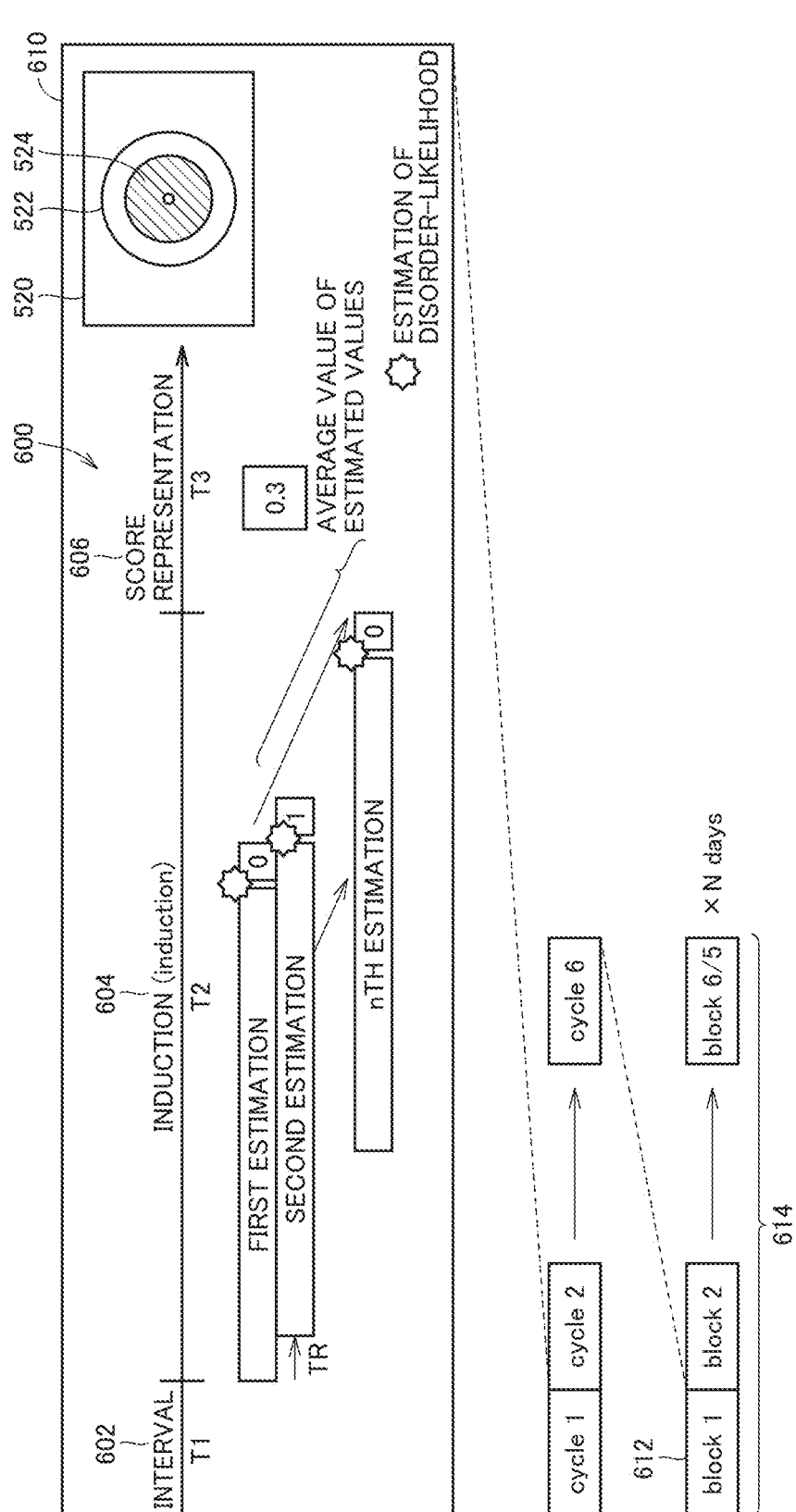
FIG. 19 is a diagram for illustrating a technique for neurofeedback training with the estimation model determined by the estimation method according to the present embodiment.

FIG. 19 is a diagram for illustrating a technique for neurofeedback training with the estimation model determined by the estimation method according to the present embodiment. Referring to FIG. 19, according to scheduling of training (for one day), a set 614 composed of a plurality of blocks 612 is carried out over a plurality of days. Each of blocks 612 includes a plurality of cycles 600. Each of cycles 600 includes a series of processes composed of an interval 602 (a duration T1), an induction period 604 (a duration T2), and a representation period 606 (a duration T3).

Interval 602 corresponds to an intermission following a previous cycle 600. Induction period 604 corresponds to a period for which the subject is more conscious of use of the brain for calculation, association, meditation, or the like for achieving assessment as a higher score, on the subject's own will or in response to an external instruction. Representation period 606 corresponds to a period for which a score calculated from the subject during induction period 604 is shown.

During induction period 604, disorder-likelihood of the subject is estimated based on EEG measurement data measured by EEG from the subject. During induction period 604, estimation of disorder-likelihood of the subject may be repeated a plurality of times. Since the result of estimation (0 or 1) of disorder-likelihood is calculated a plurality of times, the score representing the degree of disorder-likelihood of the subject during induction period 604 can be calculated by averaging the results.

For example, when an estimation model in which "0" means being healthy is adopted, the score representing the degree of disorder-likelihood of the subject is preferably smaller. Score representation 520 in accordance with the calculated score is provided to the subject. In score representation 520, as the score is smaller, score circle 524 is closer to reference circle 522.

The subject is rewarded with money or the like in accordance with the score. By being motivated by such a reward, the subject tries to make a higher score.

For example, approximately five seconds is set as duration T1 of interval 602. For example, approximately fifty to seventy seconds is set as duration T2 of induction period 604. For example, approximately five seconds is set as duration T3 of representation period 606.

In an example below, two disorders of interest, that is, schizophrenia (SCZ) (see NPL 3) and depression (MDD) (see NPL 4), were assumed.

A sampling frequency in EEG was set to 500 Hz, and EEG measurement data was processed to remove an artifact (a specific independent component of the subject extracted in advance).

A length (window size) of EEG measurement data for estimation of disorder-likelihood was set to an integral multiple of emission period TR of RF pulses in fMRI. More specifically, for schizophrenia (SCZ), the length was set to 16 TR (2.45 seconds×16=39.2 seconds), and for depression (MDD), the length was set to 20 TR (2.45 seconds×20=49 seconds).

Accordingly, duration T2 of induction period 604 for schizophrenia (SCZ) was set to seventy seconds, and duration T2 of induction period 604 for depression (MDD) was set to eighty-five seconds.

FIG. 20 is a diagram showing an exemplary result of neurofeedback training in connection with schizophrenia (SCZ). FIG. 20 (A) shows an experimental example of WLS which is the score representing disorder-likelihood to be estimated before and after training. FIG. 20 (B) shows an experimental example of a schizotypal personality questionnaire (SPQ) before and after training. SPQ represents an exemplary schizophrenia-like score. FIG. 20 (C) shows an experimental example of an n-back task before and after training.

"A" to "I" in FIGS. 20 (A) and (B) represent subjects. A smaller value of WLS shown in FIG. 20 (A) and a smaller value of SPQ shown in FIG. 20 (B) mean amelioration of a symptom. Though a significant result is not exhibited in WLS shown in FIG. 20 (A), a tendency of improvement owing to training is observed in SPQ shown in FIG. 20 (B).

The n-back task shown in FIG. 20 (C) is a test for assessing capability (a cognition function) to remember information presented N times earlier. A result in the n-back task is shown with a score "d prime." A larger value of d prime means improvement in cognition function. FIG. 20 (C) shows a result in an example where N was set to 2, 3, and 4 (N=2, 3, 4). A tendency of improvement owing to training is observed in the n-back task shown in FIG. 20 (C). In particular, in a 4-back test, significant change in a paired t-test is observed.

FIG. 21 is a diagram showing an exemplary result of neurofeedback training in connection with depression (MDD). FIG. 21 (A) shows an experimental example of WLS which is the score representing disorder-likelihood to be estimated before and after training. FIG. 21 (B) shows an experimental example of the Beck depression inventory (BDI) and the self-rating depression scale (SDS) before and after training. BDI and SDS are exemplary scores of a depression-like symptom. FIG. 21 (C) shows an experimental example of achievement in an n-back task before and after training.

"A" to "G" in FIGS. 21 (A) and (B) represent subjects. A smaller value of WLS shown in FIG. 21 (A) and smaller values of BDI and SDS shown in FIG. 21 (B) mean amelioration of a symptom. According to the exemplary results shown in FIGS. 21 (A) and (B), a tendency of improvement owing to training is observed. According to the exemplary result shown in FIG. 21 (C), a tendency of improvement in the n-back task owing to training is also observed.

(j4: Long-Term Effect of Neurofeedback Training)

Exemplary assessment of a long-term effect including a result in follow-up (FU) one to two months after the end of neurofeedback training will now be described.

Figure 22:
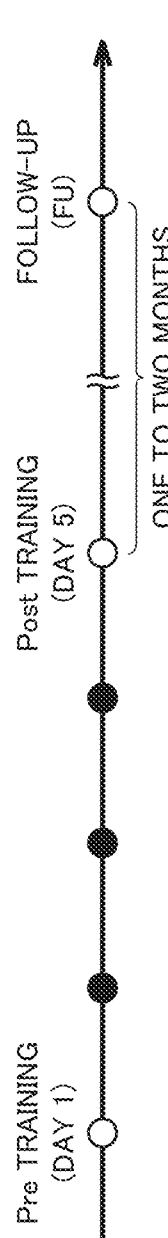
FIG. 22 is a diagram showing an exemplary procedure for assessing a long-term effect of neurofeedback training with the estimation model determined by the estimation method according to the present embodiment.

FIG. 22 is a diagram showing an exemplary procedure for assessing a long-term effect of neurofeedback training with the estimation model determined by the estimation method according to the present embodiment.

Referring to FIG. 22, training was conducted for three days, and measurement (calculation of the score) was conducted on a day preceding a training period (Pretraining), on a day following the training period (Posttraining), and on a follow-up (FU) day one to two months after the training period.

FIG. 23 is a diagram showing an exemplary long-term effect of neurofeedback training in connection with depression (MDD). FIG. 23 (A) shows an experimental example of WLS. FIG. 23 (B) shows an experimental example of BDI. FIG. 23 (C) shows an experimental example of RRS which is a score representing a frequency of rumination. A smaller value of RRS can be determined as indicating a preferred state.

Each of FIG. 23 (A) to (C) shows variation in score of each subject with a line graph and shows variation in average score of all subjects with a bar graph.

The WLS shown in FIG. 23 (A) can generally be concluded as being significant as the score representing disorder-likelihood, although there is variation among individual subjects.

For BDI shown in FIG. 23 (B), a low state is maintained at both of timing immediately after training (Post) and timing one to two months later (FU), which suggests that the effect of training lasts for a long time. FIG. 23 (B) shows also a sub score used for calculation of BDI. The sub score also exhibits the tendency similar to the tendency of BDI.

For RRS shown in FIG. 23 (C), a low state is maintained at both of timing immediately after training (Post) and timing one to two months later (FU), which suggests that the effect of training lasts for a long time. FIG. 23 (C) shows also a sub score used for calculation of RRS. The sub score also exhibits the tendency similar to the tendency of RRS.

Figure 24:
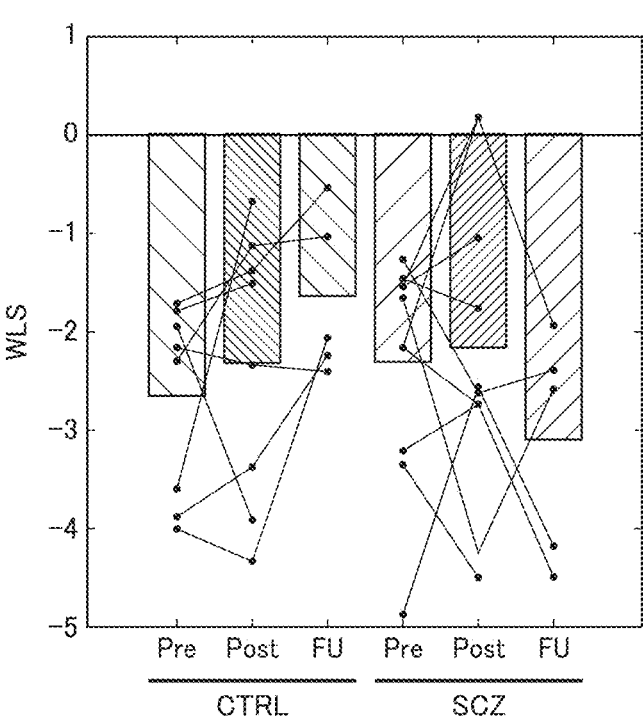
FIG. 24 is a diagram showing an exemplary long-term effect of neurofeedback training in connection with schizophrenia (SCZ).

FIG. 24 is a diagram showing an exemplary long-term effect of neurofeedback training in connection with schizophrenia (SCZ). FIG. 24 shows variation in WLS of each subject with a line graph and shows variation in averaged score of WLS of all subjects with a bar graph.

In FIG. 24, "CTRL" represents a result of a control group. The control group represents a set of subjects who conducted training with the use, as feedback information, of information on others prepared in advance rather than information from target persons. In other words, the experimental example of the control group shows a result of training in which the subject conducted training presuming that the training was based on the brain activity of the subject himself/herself in spite of the fact that the brain activity of the subject was not referred to. This is also applicable to experimental examples below.

The WLS shown in FIG. 24 is significantly different from that of the control group, although there is variation among individual subjects, and the WLS exhibits a tendency of improvement owing to training.

(j5: Effect of Neurofeedback Training)

An exemplary effect of neurofeedback training with a control group being defined as a benchmark will now be described.

Figure 25:
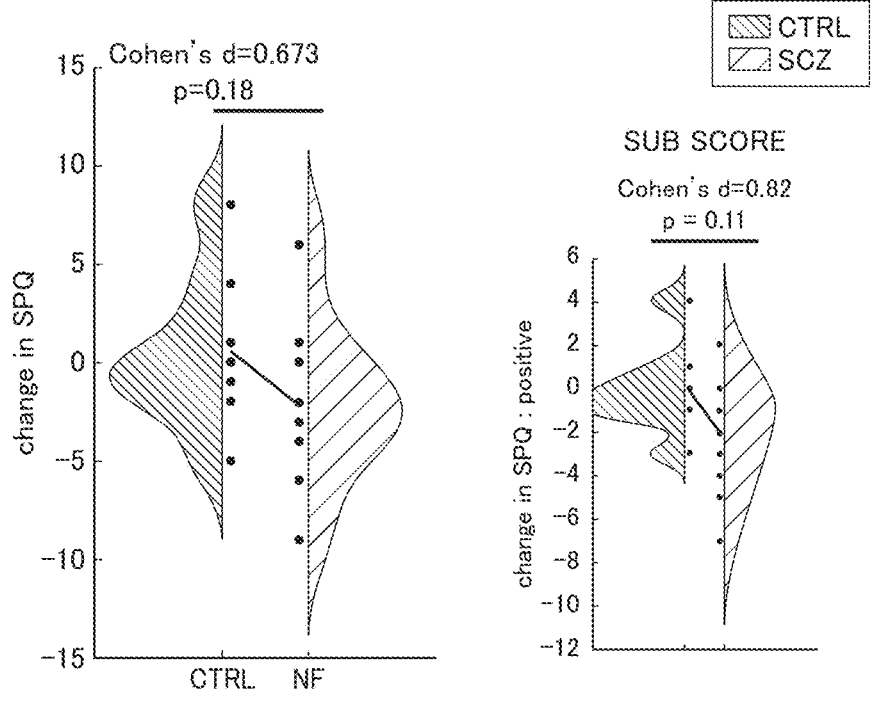
FIG. 25 is a diagram showing an effect of neurofeedback training in connection with schizophrenia (SCZ) as compared with a control group.

FIG. 25 is a diagram showing an effect of neurofeedback training in connection with schizophrenia (SCZ) as compared with the control group. The ordinate of the graph shown in FIG. 25 represents change (Post-Pre) in value before and after neurofeedback.

It can be seen that the control group (CTRL) is distributed around a point where values before and after training are not varied (a value on the ordinate is zero), whereas an appropriately trained group is distributed around a point on a negative side (that is, the value of SPQ became smaller after training). FIG. 25 also shows a sub score used for calculation of SPQ. The sub score also exhibits the tendency similar to the tendency of SPQ.

The SPQ shown in FIG. 25 also exhibits a significant difference from that of the control group and exhibits the tendency of improvement owing to training.

FIG. 26 is another diagram showing an effect of neurofeedback training in connection with schizophrenia (SCZ) as compared with the control group. The ordinate of the graph shown in each of FIG. 26 (A) to (D) represents change (Post-Pre) in value before and after neurofeedback. Each of FIG. 26 (A) to (D) shows an experimental example of the score of the cognition function.

More specifically, FIG. 26 (A) shows an experimental example in an n-back task (N=2) and FIG. 26 (B) shows an experimental example in an n-back task (N=4). In each experimental example, a control group (CTRL) is distributed around a point where values before and after training are not varied (a value on the ordinate is zero), whereas an appropriately trained group is distributed around a point on a positive side (that is, the value of d prime became larger after training).

FIGS. 26 (C) and (D) shows exemplary assessment of the cognition function with the use of Cambridge neuropsychological test automated battery (CANTAB) (see NPL 5 or the like). More specifically, rapid visual information processing (RVP) is assessed. A schizophrenic has been reported to be lower in sustained attention function.

A' and p(Hit) are outputted as the scores. Larger values of A' and p(Hit) are preferred. For calculation of these scores, software called "CANTAB® [Cognitive assessment software]. Cambridge Cognition (2019). All rights reserved. www.cantab.com" was used.

It can be seen in each experimental example that the control group (CTRL) is distributed around a point where values before and after training are not varied (a value on the ordinate is zero), whereas an appropriately trained group is distributed around a point on a positive side (that is, the values of A' and p(Hit) became larger after training).

As shown in FIGS. 25 and 26, possibility of amelioration of a symptom owing to training tends to strongly be suggested.

(j6: Specificity of Effect of Neurofeedback Training)

Though neurofeedback training itself achieves a non-specific effect such as a learning effect, achievement of a specific effect exceeding such a non-specific effect by neurofeedback training with the estimation model determined by the estimation method according to the present embodiment will be described with reference to an experimental example.

Figure 27:
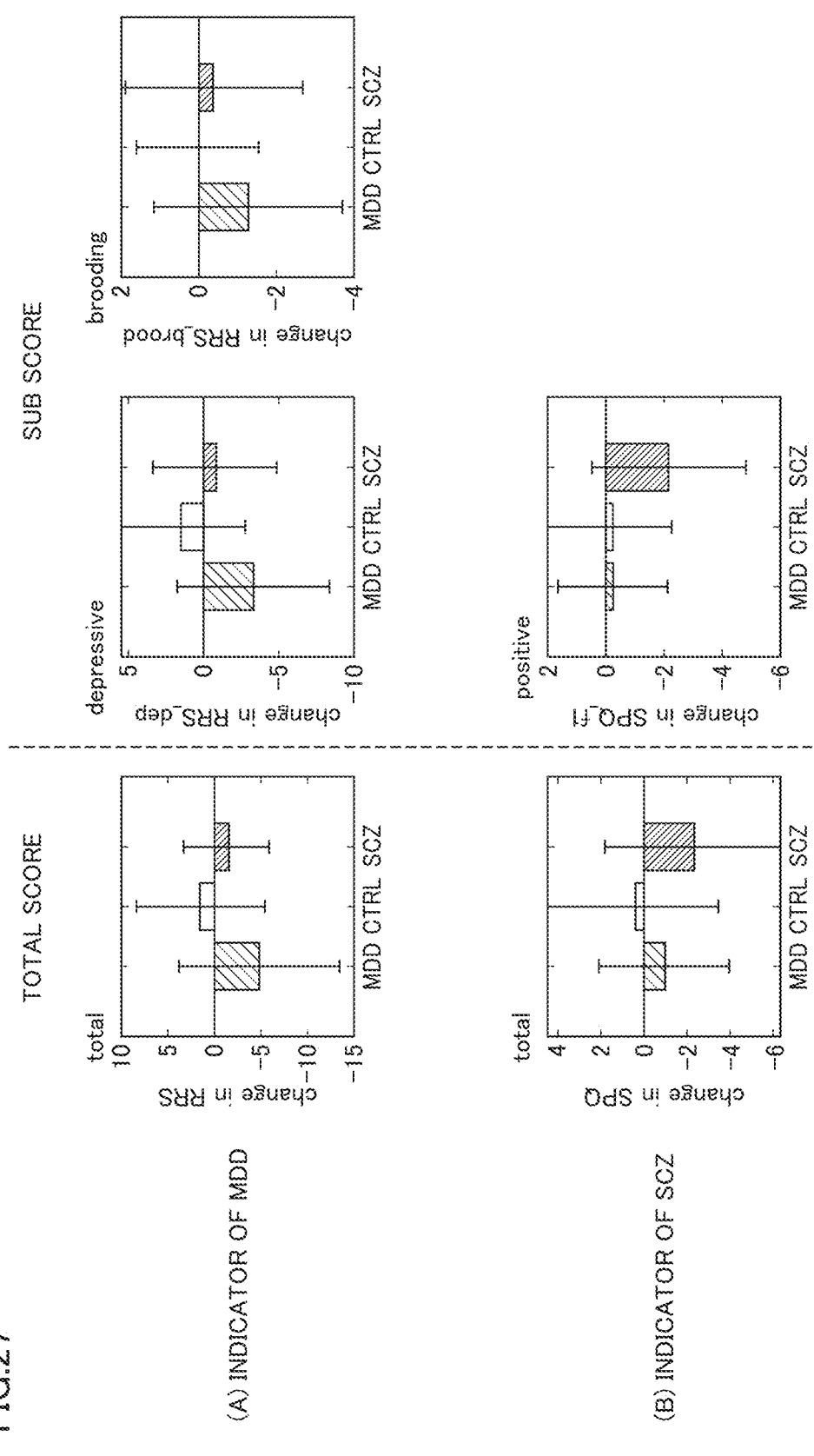
FIG. 27 is a diagram showing an experimental example for assessing specificity of the effect of neurofeedback training.

FIG. 27 is a diagram showing an experimental example for assessing specificity of the effect of neurofeedback training. FIG. 27 (A) shows exemplary change in RRS and sub score as a psychological indicator in connection with depression (MDD). FIG. 27 (B) shows exemplary change in SPQ and sub score as a psychological indicator in connection with schizophrenia (SCZ).

In FIGS. 27 (A) and (B), "MDD" represents a group trained with the estimation model (depression estimation model) determined based on EEG measurement data in connection with depression (MDD) and "SCZ" represents a group trained with the estimation model (schizophrenia estimation model) determined based on EEG measurement data in connection with schizophrenia (SCZ). "CTRL" represents a control group.

It can be seen in connection with the psychological indicator of depression (MDD) shown in FIG. 27 (A) that specific change in each of RRS (total score) and the sub score occurred in the group (MDD) trained with the depression estimation model.

It can be seen in connection with the psychological indicator of schizophrenia (SCZ) shown in FIG. 27 (B) that specific change in each of SPQ (total score) and the sub score occurred in the group (SCZ) trained with the schizophrenia estimation model.

FIG. 28 is a diagram showing another experimental example for assessing specificity of the effect of neurofeedback training. FIG. 28 shows exemplary variation in cognition function. FIG. 28 (A) shows an experimental example of an n-back task (N=3) and FIG. 28 (B) shows an experimental example of an n-back task (N=4).

The experimental example shown in FIG. 28 (A) exhibits a tendency of improvement in cognition function owing to training with any of the depression estimation model and the schizophrenia estimation model. The experimental example shown in FIG. 28 (B) exhibits a tendency of significant improvement in cognition function owing to training with the schizophrenia estimation model.

These experimental examples exhibit the tendency of improvement in cognition function owing to neurofeedback training with the estimation model determined by the estimation method according to the present embodiment, and the higher tendency of improvement with the use of schizophrenia estimation model is observed.

K. Advantage

With the estimation system according to the present embodiment, a brain function expressed in a plurality of brain networks and any disorder associated with the plurality of brain networks can be estimated in a more simplified manner with the use of EEG measurement data.

With the estimation system according to the present embodiment, since only a feature value effective for estimation of disorder-likelihood in EEG measurement data is used in the estimation model, dimensions of the estimation model can be compressed and reduced so that an amount of computation involved with estimation of disorder-likelihood can be reduced and estimation of disorder-likelihood can be accelerated.

With the estimation system according to the present embodiment, disorder-likelihood of any disorder associated with a plurality of brain networks can be estimated, so that neurofeedback training can be applied to various disorders.

With the estimation system according to the present embodiment, since the estimation model can be determined with the use of measurement data obtained by simultaneously conducting EEG and fMRI in a resting state, a task does not have to be provided to a subject in EEG and fMRI simultaneous measurement and hence burdens imposed on the subject in construction of the estimation model can be lessened.

Neurofeedback training provided by the estimation system according to the present embodiment provides a tendency of amelioration of some disorders and the tendency of amelioration is maintained for a long time.

The estimation model used in neurofeedback training provided by the estimation system according to the present embodiment exhibits specificity depending on target and is generated in accordance with a disorder.

It should be understood that the embodiment disclosed herein is illustrative and non-restrictive in every respect. The scope of the present invention is defined by the terms of the claims rather than the description of the embodiment above and is intended to include any modifications within the scope and meaning equivalent to the terms of the claims.

REFERENCE SIGNS LIST 1 estimation system; 2 brain activity training apparatus; 11 feature value information; 12 weight parameter; 13 adder; 14 binarizer; 20 EEG measurement data; 22 time waveform of power; 24 time waveform of EEG time correlation; 26 window; 30 fMRI measurement data; 32 BOLD signal; 34 time waveform of BOLD time correlation; 38 disorder-likelihood label; 100, 500 processing apparatus; 102 processor; 104 main storage; 106 control interface; 108 network interface; 110, 352 input unit; 112, 353 display unit; 120 secondary storage; 121 estimation model determination program; 122 estimation program; 124 estimation model parameter; 150, 160, 550 preprocessing module; 152, 162, 552 time correlation calculation module; 164 WLS calculation module; 166, 556 binarization module; 168 model estimation module; 200 EEG apparatus; 202 multiplexer; 204 noise filter; 206 A/D converter; 208, 354 storage; 210, 358 interface; 220 sensor; 222 cable; 300 fMRI apparatus; 302 reception coil; 310 magnetic field application mechanism; 312 static magnetic field generation coil; 314 gradient magnetic field generation coil; 316 emitter; 318 bed; 320 driver; 322 static magnetic field power supply; 324 gradient magnetic field power supply; 326 signal transmitter; 328 signal receiver; 330 bed driver; 350 data processing unit; 351 control unit; 356 image processing unit; 357 data collector; 400 server apparatus; 402 subject data; 502 storage device; 510 display device; 520 score representation; 522 reference circle; 524 score circle; 554 weighted sum calculation module; 558 estimation model obtaining module; 560 representation control module; 600 cycle; 602 interval; 604 induction period; 606 representation period; 612 block; 614 set

The invention claimed is:

1. An estimation system with one or more processors configured to:
    obtain, from an electroencephalograph, brain wave measurement data and, from a functional magnetic resonance imaging device, functional magnetic resonance imaging measurement data simultaneously measured from a subject, the brain wave measurement data including time waveforms for a plurality of channels corresponding to respective ones of a plurality of sensors arranged in a head of the subject;
    calculate first functional connectivity for each channel combination based on correlation between channels included in the brain wave measurement data;
    calculate second functional connectivity for each brain network based on correlation between regions of interest included in the functional magnetic resonance imaging measurement data;
    calculate a disorder-likelihood label by calculating a score representing disorder-likelihood to be estimated based on a plurality of second functional connectivities; and
    determine an estimation model for estimating the disorder-likelihood based on prescribed first functional connectivity by machine learning using the first functional connectivity for each channel combination and the disorder-likelihood label; and
    outputting a signal including the disorder-likelihood to a presentation apparatus.

2. The estimation system according to claim 1, further configured to estimate the disorder-likelihood of the subject by inputting the brain wave measurement data measured from the subject into the estimation model.

3. The estimation system according to claim 2, further configured to calculate a second score in accordance with the estimated disorder-likelihood of the subject and present to the subject, information in accordance with the calculated second score.

4. The estimation system according to claim 3, wherein the estimation model is prepared for each disorder, and an estimation model corresponding to a disorder that manifests in the subject is applied to the subject.

5. The estimation system according to claim 1, wherein change in symptom of the subject is assessed based on a second score in accordance with an estimated disorder-likelihood of the subject.

6. The estimation system according to claim 1, wherein calculating the disorder-likelihood label comprises calculating the score representing the disorder-likelihood based on a sum of results of multiplication of the plurality of second functional connectivities brought in correspondence with disorder-likelihood to be estimated by respective corresponding weight parameters.

7. The estimation system according to claim 6, wherein calculating the disorder-likelihood label comprises normalizing the score representing the disorder-likelihood and subject the normalized score to threshold processing.

8. The estimation system according to claim 1, wherein the estimation model includes information for selecting first functional connectivity to be used for estimation among first functional connectivities for each channel combination and a weight parameter brought in correspondence with the selected first functional connectivity.

9. The estimation system according to claim 1, wherein calculating the first functional connectivity is based on a correlation value between time waveforms in a section included in a window set in common for time waveforms of brain waves in two channels of interest.

10. The estimation system according to claim 1, wherein calculating the first functional connectivity comprises calculating the first functional connectivity for each frequency band included in the brain wave measurement data and/or for each window size of a set window.

11. The estimation system according to claim 10, further configured to determine in advance in accordance with the subject, the frequency band included in the brain wave measurement data to be inputted to the estimation model and/or the window size.

12. The estimation system according to claim 1, wherein calculating the second functional connectivity is based on a correlation value between time waveforms in a section included in a window set in common for time waveforms indicating amounts of activities in two regions of interest.

13. An estimation method comprising:

obtaining, from an electroencephalograph, brain wave measurement data and, from a functional magnetic resonance imaging device, functional magnetic resonance imaging measurement data simultaneously measured from a subject, the brain wave measurement data including time waveforms for a plurality of channels corresponding to respective ones of a plurality of sensors arranged in a head of the subject;

calculating first functional connectivity for each channel combination based on correlation between channels included in the brain wave measurement data;

calculating second functional connectivity for each brain network based on correlation between regions of interest included in the functional magnetic resonance imaging measurement data;

calculating a disorder-likelihood label by calculating a score representing disorder-likelihood to be estimated based on a plurality of second functional connectivities;

determining an estimation model for estimating the disorder-likelihood based on prescribed first functional connectivity by machine learning using the first functional connectivity for each channel combination and the disorder-likelihood label; and outputting a signal including the disorder-likelihood to a presentation apparatus.

14. A non-transitory storage medium storing a program thereon, when executed by one or more processors, causing the one or more processors to perform:

obtaining, from an electroencephalograph, brain wave measurement data and, from a functional magnetic resonance imaging device, functional magnetic resonance imaging measurement data simultaneously measured from a subject, the brain wave measurement data including time waveforms for a plurality of channels corresponding to respective ones of a plurality of sensors arranged in a head of the subject;

calculating first functional connectivity for each channel combination based on correlation between channels included in the brain wave measurement data;

calculating second functional connectivity for each brain network based on correlation between regions of interest included in the functional magnetic resonance imaging measurement data;

calculating a disorder-likelihood label by calculating a score representing disorder-likelihood to be estimated based on a plurality of second functional connectivities;

determining an estimation model for estimating the disorder-likelihood based on prescribed first functional connectivity by machine learning using the first functional connectivity for each channel combination and the disorder-likelihood label; and outputting a signal including the disorder-likelihood to a presentation apparatus.

15. A trained estimation model for estimating disorder-likelihood of a subject based on brain wave measurement data measured from the subject, processing for constructing the estimation model comprising:

obtaining, from an electroencephalograph, brain wave measurement data and, from a functional magnetic resonance imaging device, functional magnetic resonance imaging measurement data simultaneously measured from the subject, the brain wave measurement data including time waveforms for a plurality of channels corresponding to respective ones of a plurality of sensors arranged in a head of the subject;

calculating first functional connectivity for each channel combination based on correlation between channels included in the brain wave measurement data;

calculating second functional connectivity for each brain network based on correlation between regions of interest included in the functional magnetic resonance imaging measurement data;

calculating a disorder-likelihood label by calculating a score representing disorder-likelihood to be estimated based on a plurality of second functional connectivities; and determining the estimation model by machine learning using the first functional connectivity for each channel combination and the disorder-likelihood label; and outputting a signal including a disorder likelihood to a presentation apparatus.

16. A brain activity training apparatus for conducting neurofeedback training, the brain activity training apparatus comprising:

a storage device where an estimation model for estimating disorder-likelihood of a subject generated before the neurofeedback training is conducted is stored;

an electroencephalograph configured to measure brain wave measurement data of the subject in the neurofeedback training, the brain wave measurement data including first time waveforms for a plurality of channels corresponding to respective ones of a plurality of sensors arranged in a head of the subject;

a presentation apparatus; and a processing apparatus configured to calculate, in the neurofeedback training, disorder-likelihood of the subject with the estimation model based on measurement data from the electroencephalograph and outputs a signal for representation corresponding to the disorder-likelihood to the presentation apparatus, wherein the estimation model is generated by processing for obtaining, from the electroencephalo-graph, the brain wave measurement data and, from a functional magnetic resonance imaging device, functional magnetic resonance imaging measurement data simultaneously measured from the subject, the simultaneously measured brain wave measurement data including a second time waveform for each channel corresponding to each channel of the brain wave measurement data measured in the neurofeed-back training, processing for calculating first functional connectivity for each channel combination based on correlation between channels included in the brain wave measurement data, processing for calculating second functional connectivity for each brain network based on correlation between regions of interest included in the functional magnetic resonance imaging measurement data, processing for calculating a disorder-likelihood label by calculating a score representing disorder-likelihood to be estimated based on a plurality of second functional connectivities, processing for determining the estimation model by estimating the disorder-likelihood based on prescribed first functional connectivity by machine learning using the first functional connectivity for each channel combination and the disorder-likelihood label; and processing for outputting the disorder-likelihood by outputting a signal including the disorder-likelihood to the presentation apparatus.

17. A brain activity training method for conducting neu-rofeedback training, the brain activity training method comprising:

obtaining an estimation model for estimating disorder-likelihood of a subject generated before the neurofeed-back training is conducted;

measuring brain wave measurement data of the subject in the neurofeedback training, the brain wave measure-ment data including first time waveforms for a plurality of channels corresponding to respective ones of a plurality of sensors arranged in a head of the subject; and calculating, in the neurofeedback training, disorder-like-lihood of the subject with the estimation model based on the brain wave measurement data and outputting a signal for representation corresponding to the disorder-likelihood to a presentation apparatus, wherein the obtaining an estimation model includes obtaining, from an electroencephalograph, the brain wave measurement data and, from a functional mag-netic resonance imaging device, functional magnetic resonance imaging measurement data simultane-ously measured from the subject, the simultaneously measured brain wave measurement data including a second time waveform for each channel correspond-ing to each channel of the brain wave measurement data measured in the neurofeedback training, calculating first functional connectivity for each chan-nel combination based on correlation between chan-nels included in the brain wave measurement data, calculating second functional connectivity for each brain network based on correlation between regions of interest included in the functional magnetic reso-nance imaging measurement data, calculating a disorder-likelihood label by calculating a score representing disorder-likelihood to be esti-mated based on a plurality of second functional connectivities, determining the estimation model by estimating the disorder-likelihood based on prescribed first func-tional connectivity by machine learning using the first functional connectivity for each channel com-bination and the disorder-likelihood label; and outputting a signal including a disorder likelihood to a presentation apparatus.

18. A non-transitory storage medium storing thereon a brain activity training program for conducting neurofeed-back training, when executed by one or more processors, the brain activity training program causing the one or more processors to perform:

storing an estimation model for estimating disorder-like-lihood of a subject generated before the neurofeedback training is conducted;

obtaining brain wave measurement data of the subject in the neurofeedback training, the brain wave measure-ment data including first time waveforms for a plurality of channels corresponding to respective ones of a plurality of sensors arranged in a head of the subject; and calculating, in the neurofeedback training, disorder-like-lihood of the subject with the estimation model based on the brain wave measurement data and outputting a signal for representation corresponding to the disorder-likelihood to a presentation apparatus, wherein the estimation model is generated by processing for obtaining, from an electroencephalo-graph, the brain wave measurement data and, from a functional magnetic resonance imaging device, func-tional magnetic resonance imaging measurement data simultaneously measured from the subject, the simultaneously measured brain wave measurement data including a second time waveform for each channel corresponding to each channel of the brain wave measurement data measured in the neurofeed-back training, processing for calculating first functional connectivity for each channel combination based on correlation between channels included in the brain wave mea-surement data, processing for calculating second functional connec-tivity for each brain network based on correlation between regions of interest included in the functional magnetic resonance imaging measurement data, processing for calculating a disorder-likelihood label by calculating a score representing disorder-likeli-hood to be estimated based on a plurality of second functional connectivities, processing for determining the estimation model by estimating the disorder-likelihood based on pre-scribed first functional connectivity by machine learning using the first functional connectivity for each channel combination and the disorder-likeli-hood label; and outputting a signal including a disorder likelihood to a presentation apparatus.

* * * * *